United States Patent [19]
Zasloff

[11] Patent Number: 6,143,738
[45] Date of Patent: Nov. 7, 2000

[54] THERAPEUTIC USES FOR AN AMINOSTEROL COMPOUND

[75] Inventor: Michael Zasloff, Merion Station, Pa.

[73] Assignee: Magainin Pharmaceuticals, Inc., Plymouth, Pa.

[21] Appl. No.: 08/857,288

[22] Filed: May 16, 1997

Related U.S. Application Data

[63] Continuation-in-part of application No. 08/487,443, Jun. 7, 1995, Pat. No. 5,847,172.
[60] Provisional application No. 60/017,627, May 17, 1996, and provisional application No. 60/029,541, Nov. 1, 1996.

[51] Int. Cl.$^7$ .................................................. A61K 31/56
[52] U.S. Cl. .......................... 514/181; 514/178; 514/182
[58] Field of Search ................................... 514/182, 181, 514/178

[56] References Cited

U.S. PATENT DOCUMENTS

| | | |
|---|---|---|
| 3,016,390 | 1/1962 | Counsell . |
| 3,370,070 | 2/1968 | Klimstra et al. . |
| 4,220,598 | 9/1980 | Hixson, Jr. et al. . |
| 4,372,888 | 2/1983 | Hjelmeland . |
| 4,425,273 | 1/1984 | Iida et al. . |
| 4,514,393 | 4/1985 | Castagnola et al. . |
| 4,545,938 | 10/1985 | Mosbach et al. . |
| 4,550,163 | 10/1985 | Voss et al. . |
| 4,565,811 | 1/1986 | Di Schiena . |
| 4,771,042 | 9/1988 | Braughler et al. . |
| 4,793,948 | 12/1988 | Hatono et al. . |
| 4,966,897 | 10/1990 | Angelastro et al. . |
| 4,994,443 | 2/1991 | Folkman et al. . |
| 5,001,116 | 3/1991 | Folkman et al. . |
| 5,004,737 | 4/1991 | Kim et al. . |
| 5,039,529 | 8/1991 | Bergendal et al. . |
| 5,057,509 | 10/1991 | Pellicciari et al. . |
| 5,061,701 | 10/1991 | Pellicciari et al. . |
| 5,063,222 | 11/1991 | Komoto et al. . |
| 5,075,464 | 12/1991 | Blohm et al. . |
| 5,135,919 | 8/1992 | Folkman et al. . |
| 5,192,756 | 3/1993 | Zasloff et al. . |
| 5,250,524 | 10/1993 | Kramer et al. . |
| 5,637,691 | 6/1997 | Frye et al. . |
| 5,763,430 | 6/1998 | Zasloff ..................................... 514/182 |
| 5,840,936 | 11/1998 | Zasloff et al. ........................... 514/182 |

FOREIGN PATENT DOCUMENTS

| | | |
|---|---|---|
| 0 394 971 A1 | 10/1990 | European Pat. Off. . |
| 0 466 315 A2 | 1/1992 | European Pat. Off. . |
| 2 361 899 | 3/1978 | France . |
| 1 565 351 | 4/1980 | United Kingdom . |
| WO87/02367 | 4/1987 | WIPO . |
| WO91/19731 | 12/1991 | WIPO . |
| WO93/25197 | 12/1993 | WIPO . |
| WO94/19366 | 9/1994 | WIPO . |
| WO94/20520 | 9/1994 | WIPO . |
| WO95/24415 | 9/1995 | WIPO . |
| WO96/40151 | 12/1996 | WIPO . |
| WO96/40728 | 12/1996 | WIPO . |

OTHER PUBLICATIONS

McKenna, James et al., "Bis–steroids as Potential Enzyme Models: Perylene Solubilisation and Dye Spectral Changes with Aqueous Solutions of Some Derivatives of Conessine and Cholic Acid;" *J.C.S. Chem. Comm.*, 1977, pp. 809–811.
Crum, Rosa et al., "A New Class of Steroids Inhibits Angiogenesis in the Presence of Heparin or a Heparin Fragment," Science, vol. 230, 1985, pp. 1375–1378.
Derwent Abstract No. 86–085704, "Anticancer Drug Contains Shark Liver Extract Doxorubicin," 1984.
Biosis No. 82085007, "Studies on Antitumor Activity of Squalene and Its Related Compounds," Yakugaku Zasshi, 1986.
Chemical Abstract No. 111: 17264, "Increasing the Therapeutic Efficacy of Antitumor Drugs," 1989.
Bellini, A.M. et al., "Antimicrobial Activity of Basic Cholane Derivatives, Part IX," Arch. Pharm. (Weinheim) 323, 201–205 (1990).
Bellini, Anna M. et al., Antimicrobial Activity of Basic Cholane Derivatives. X. Synthesis of 3α– and 3β–amino–5β–cholan–24–oic Acids, *Steroids*, vol. 56, Jul. 1991, pp. 395–397.
Gagliardi, A., et al., "Inhibition of Angiogenesis by Antiestrogens," *Cancer Research*, 53, pp. 533–535, Feb. 1, 1993.
Moore, Karen S. et al., "Squalamine: An Aminosterol Antibiotic from the Shark," *Proc. Natl. Acad. Sci.*, USA, vol. 90, pp. 1354–1358, Feb. 1993.
Wehrli, S. et al., "Structure of the Novel Steroidal Antibiotic Squalamine Determined by Two–Dimensional NMR Spectroscopy," *Steroids*, vol. 58, No. 8, Aug. 1993, pp. 370–378.
Children's Hospital of Pennsylvania, "Aminosterol Antibiotic;" Current Opinion in Therapeutic Patents Sep. 1993, pp. 1369–1370.
Auerbach, R. et al., "Angiogenesis Inhibition: A Review;" *Pharmac. Ther.*, vol. 63, pp. 265–311, 1994.

(List continued on next page.)

*Primary Examiner*—Jerome D. Goldberg
*Attorney, Agent, or Firm*—Morgan, Lewis & Bockius LLP

[57] ABSTRACT

A pharmaceutical composition includes, as an active ingredient, a compound according to formula 1436 as shown in FIG. 1, or a pharmaceutically acceptable salt thereof, and a pharmaceutically acceptable carrier or excipient. Various pharmaceutical products may be produced including this pharmaceutical composition. Such pharmaceutical products may be used for the treatment of cancers, such as leukemia; inflammation; arthritis; and viruses, such as HSV. Methods for using the pharmaceutical compositions also are described. In these methods, various diseases are treated or other body functions are activated or inhibited by administering an effective amount of the pharmaceutical composition. For example, inflammation, arthritis, herpes simplex virus, melanoma, and leukemia may be treated by administering an effective amount of the pharmaceutical compositions. Viral replication, weight gain, and growth factor production can be inhibited by administering an effective amount of these pharmaceutical compositions. Appetite can be suppressed by administering an effective amount of the pharmaceutical compositions, and a diuretic effect can be produced.

16 Claims, 25 Drawing Sheets

OTHER PUBLICATIONS

Moriarty, Robert M. et al., "Synthesis of Squalamine, A Steroidal Antibiotic from the Shark," *Tetrahedron Letters*, vol. 35, No. 44, pp. 8103–8106, 1994.

Sadownik, Andrzej et al., "Rapid Construction of a Squalamine Mimic;" *J. Am. Chem. Soc.*, 1995, vol. 117, pp. 6138–6139.

"Shark Cartilage for Cancer Treatment," P&T Newsletter, Mar. 1996, pp. 159–160.

"Designing Therapies that Target Tumor Blood Vessels;" *Science*, vol. 275, Jan. 24, 1997, pp. 482–484.

Akhter, "Squalamine, A Novel Aminosterol Antibiotic is a Specific Inhibitor of Epithelial Brush Border $Na^+/H^+$ Exchanger Isoform, NHE3," *FASEB Journal*, vol. 10, No. 3 (1996), p. A89.

Nath, "The Novel Aminosterol Antibiotics Squalamine and 1436 are Specific Inhibitors of Epithelial Brush Border $Na^+/H^+$ Exchanger (NHE) Isoform, NHE3," *Gastroenterology*, vol. 110, No. 4, Suppl. (1996), A349.

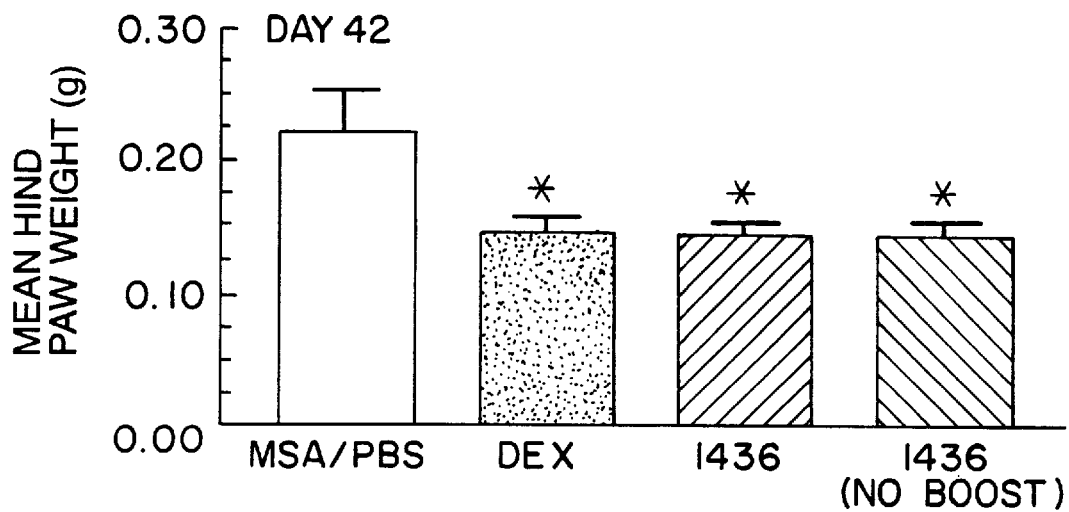
FIG. 19   MEAN ± SD
         * p < .01 (ANOVA)
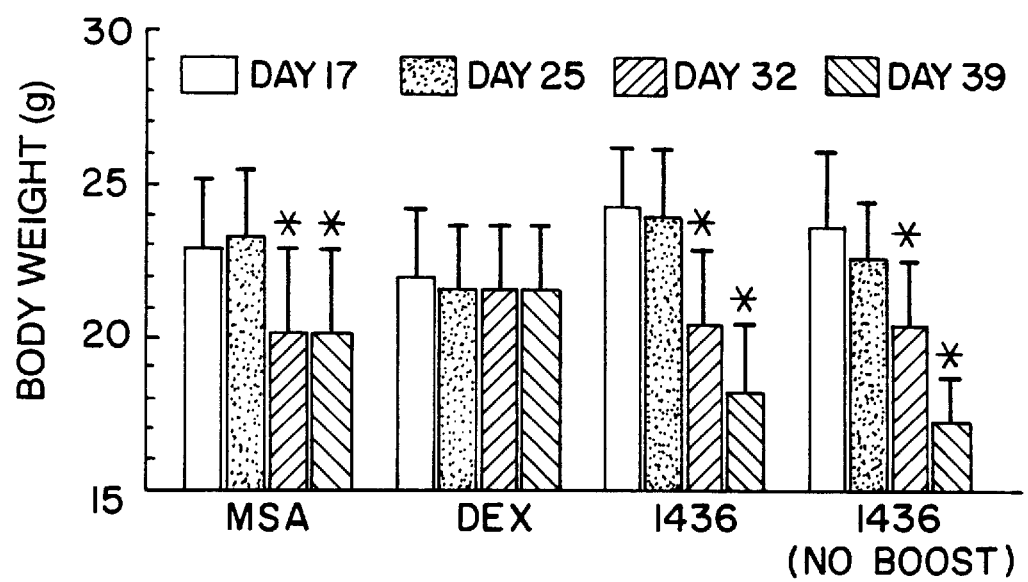
FIG. 20   MEAN ± SD
         * p < .01 VS. DAY 17

THERAPEUTIC USES FOR AN AMINOSTEROL COMPOUND

CROSS-REFERENCES TO RELATED APPLICATIONS

This application claims priority to Provisional Application Ser. No.60/017,627, filed May 17, 1996 and Provisional Application Ser. No.60/029,541, filed Nov. 1, 1996, which applications each are entirely incorporated herein by reference. This application is also a continuation-in-part of U.S. application Ser. No. 08/487,443, filed Jun. 7, 1995, now U.S. Pat. No. 5,847,172, issued Dec. 8, 1998.

BACKGROUND OF THE INVENTION

1. Information Relating to Previous Patents and Applications

Several aminosterol compositions have been isolated from the liver and stomach of the dogfish shark, *Squalus acanthias*. One important aminosterol, squalamine, is the subject of U.S. Pat. No. 5,192,756 to Zasloff, et al., which patent is entirely incorporated herein by reference. That patent describes the antibiotic properties of squalamine. Since the discovery of squalamine, several interesting properties of this compound have been discovered. For example, as described in U.S. patent appl. Ser. No. 08/416,883 (filed Apr. 20, 1995) and U.S. patent application Ser. No. 08/478,763 (filed Jun. 7, 1995), squalamine may function as an antiangiogenic agent. These patent applications are entirely incorporated herein by reference. Additional uses of squalamine (e.g., as an NHE3 inhibiting agent and as an agent for inhibiting the growth of endothelial cells) are disclosed in U.S. patent appl. Ser. No. 08/474,799 (filed Jun. 7, 1995) and U.S. patent appl. Ser. No. 08/840,706 (filed Apr. 25, 1997, entitled "Treatment of Carcinomas Using Squalamine in Combination with Other Anti-cancer Agents," in the names of Michael Zasloff and Jon Williams). These applications also are entirely incorporated herein by reference.

Methods for synthesizing squalamine have been devised, such as the methods described in WO 94/19366 (published Sep. 1, 1994) and in U.S. patent appl. Ser. No. 60/032,378. This PCT publication and the U.S. patent application are entirely incorporated herein by reference. The PCT application relates to U.S. patent appl. Ser. No. 08/023,347, which application also is entirely incorporated herein by reference. Additionally, U.S. patent appl. Ser. No. 08/474,799 also discloses squalamine isolation and synthesis techniques.

Stemming from the discovery of squalamine, other aminosterols have been discovered in the dogfish shark liver and stomach and have been investigated. One important aminosterol that has been isolated and identified has the structure shown in FIG. 1. In this application, the compound having the structure shown in FIG. 1 will be referred to as "compound 1436" or simply "1436." This compound has the general molecular formula $C_{37}H_{72}N_4O_5S$ and a calculated molecular weight of 684.53017.

Compound 1436 previously has been described in U.S. patent appl. Ser. Nos. 08/483,057; 08/479,457; and 08/487,443, each filed Jun. 7, 1995. Each of these U.S. patent applications is entirely incorporated herein by reference. These U.S. patent applications describe the structure of compound 1436 and other aminosterols, as well as processes for synthesizing and isolating compound 1436 and other aminosterols. For example, compound 1436 may be prepared from a squalamine starting material. Additional methods for synthesizing compound 1436 (as well as squalamine) are described in U.S. Provisional patent appl. Ser. No. 60/032,378, filed Dec. 6, 1996, which application is entirely incorporated herein by reference.

As further described in these patent applications, compound 1436 has a variety of interesting properties. For example, compound 1436 has been found to be capable of inhibiting mitogen-induced mouse, dog or human T-lymphocyte proliferation, as well as being capable of inhibiting the proliferation of a variety of other cells and tissues.

2. Information Relating to this Application

Compound 1436 and other aminosterol compounds isolated from the dogfish shark liver and stomach have been found to possess interesting antibiotic and anti-proliferative properties with respect to a variety of cells and tissues. These interesting properties of compound 1436 have prompted applicants to conduct further investigation into the uses and properties of this compound.

It has been found that compound 1436 has antiviral effects on several viruses. For example, compound 1436 has been found to inhibit replication of the human immunodeficiency virus ("HIV") in accepted tissue culture models. In addition to its inhibitory effect on HIV, compound 1436 also inhibits replication of the simian immunodeficiency virus ("SIV") in tissue culture. Based on these properties, applicants conclude that compound 1436 has immunomodulatory and antiviral effects. As an additional example of its antiviral activity, applicants have determined that compound 1436 is effective in inhibiting replication of the herpes simplex virus ("HSV").

In addition to its favorable antiviral activity, applicants have found that compound 1436 also has anti-proliferative effects that assist in the treatment of various types of cancer. The growth of various different types of cancer tumors is inhibited by treatment with compound 1436. Applicants have found, for example, that proliferation of human melanoma cells is inhibited by compound 1436 even after relatively short treatment times. Additionally, compound 1436 has been found to be effective in treating leukemias, such as murine acute lymphocytic leukemia (murine "ALL") and human myeloid leukemic cells growing in a mouse xenograft model.

Applicants have found still further uses for compound 1436. It has been found that delayed type immune hypersensitivity and arthritis also may be effectively treated using compound 1436. In mouse models, the use of compound 1436 was found to significantly reduce paw swelling in mice that were induced to develop arthritis.

In addition to treating various ailments and diseases, such as viral based ailments and diseases, cancers, and arthritis, compound 1436 has been found to have other favorable properties and effects. As one specific example, applicants have found that compound 1436 may be used to reduce weight gain in mammals. The weight gain of the animals in these studies was controlled due to reduction of net fluid intake. The animals continued to have normal food consumption and were apparently healthy, viable animals.

The loss of fluid upon 1436 administration was found by the inventors to involve a commensurate loss of electrolytes in animals. The compound 1436 may, therefore, be useful in therapeutic settings where diuresis is desirable, such as congestive heart failure, nephrotic syndromes, post-surgical hypervolemia, hepatic cirrhosis, cerebral edema secondary to head trauma, or lymphedema.

SUMMARY OF THE INVENTION

This invention relates to a pharmaceutical composition, including a compound according to formula 1436 as shown in FIG. 1, or a pharmaceutically acceptable salt thereof (as an active ingredient), and a pharmaceutically acceptable carrier or excipient. The invention further relates to pharmaceutical products including the pharmaceutical composition described above. Such pharmaceutical products may be provided for the treatment of cancers; leukemias; inflammation; arthritis; congestive heart failure; or viruses, such as HIV, SIV, or HSV.

This invention further relates to various methods for using the pharmaceutical compositions in accordance with the invention. In the methods according to the invention, various diseases or symptoms of diseases or ailments are treated by administering an effective amount of the above-described pharmaceutical composition. "Treat," "treated," or "treating," as used in this application may mean complete elimination of the disease, ailment, or symptoms, or it may mean reducing, suppressing, or ameliorating the severity of the disease, ailment, or symptoms. As examples, inflammation, arthritis, HIV, SIV, HSV, melanoma, and leukemia may be treated by administering an effective amount of the pharmaceutical compositions in accordance with the invention. Additionally, certain body functions may be inhibited or enhanced by administering an effective amount of the above-described pharmaceutical compositions. In this manner, tumor cell replication, weight gain, and growth factor production can be inhibited, or a diuretic effect can be produced by administering an effective amount of the pharmaceutical compositions in accordance with the invention. In another embodiment of this invention, an anti-arthritis activity can be produced by administering 1436.

BRIEF DESCRIPTION OF THE DRAWINGS

These and other advantageous aspects of the invention will be evident from the following detailed description which should be considered in conjunction with the attached drawings, wherein:

FIG. 19 shows reduced edema in 1436-treated mice in an arthritis model;

FIG. 20 shows the effect of 1436 on mouse body weight in one study;

DETAILED DESCRIPTION OF THE INVENTION

Figure 1:
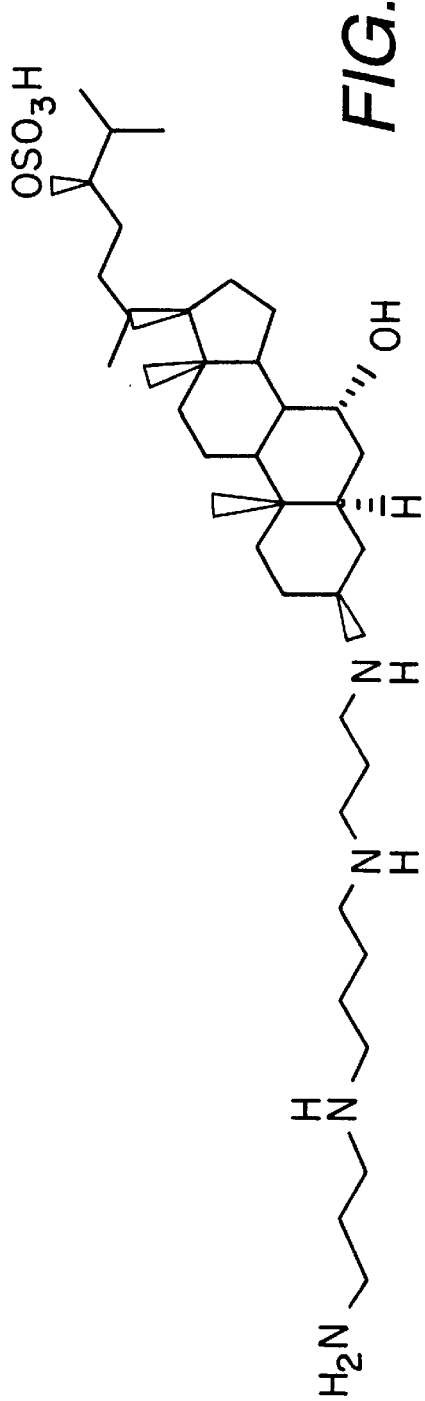
FIG. 1 illustrates the molecular structure of aminosterol 1436.
Figure 2:
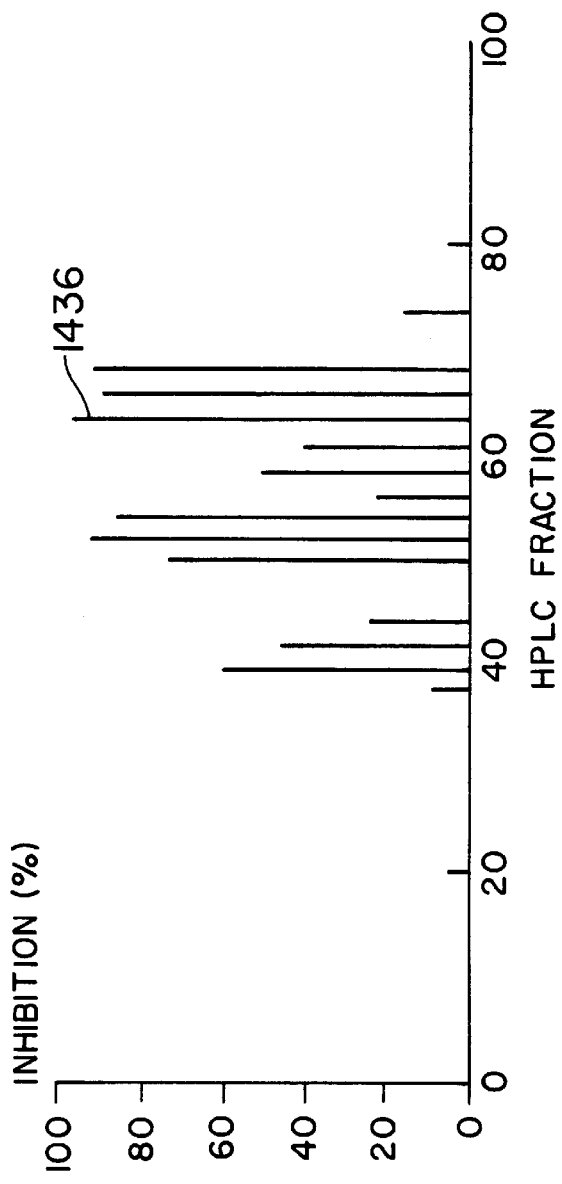
FIG. 2 illustrates the inhibition of mitosis in human T-cell lymphocytes by various materials isolated from the dogfish shark liver, including fractions containing primarily compound 1436.

As described above, compound 1436 has been discovered in and isolated from the liver and stomach of the dogfish shark. To separate the various compounds found in the liver, reverse phase high-performance liquid chromatography (HPLC) was performed. HPLC techniques are known in the art. After separation, the various HPLC fractions were tested to determine their effectiveness in inhibiting cell mitosis. FIG. 2 illustrates the inhibition of mitosis (i.e., inhibition of the "mitotic index") in human lymphocytes by the compounds that were isolated from the dogfish shark liver in the different HPLC fractions. A high percent inhibition in FIG. 2 indicates that the compound is effective in preventing or inhibiting cell duplication or replication (i.e., mitosis). In addition, some aminosterols were noted to induce changes in cell shape and (apparent) size when they were incubated in tissue culture with cell lines taken from various tissues. Such compounds may be useful in treating the many diseases and ailments that depend on cell proliferation (e.g., cancer, viral diseases, etc.) or function. Compound 1436 was isolated from the HPLC fraction of the dogfish shark liver that showed the highest mitosis inhibition level in the PHA-stimulated human T-lymphocyte cells. This fraction is labeled "1436" in FIG. 2.

Based on the information in FIG. 2, applicants conclude that compound 1436 inhibits proliferation of human T-lymphocyte cells (i.e., 1436 inhibits cell duplication or reproduction). From this observed activity, applicants believed that compound 1436 may have antiviral activities against viruses that infect lymphocytes. It has now been shown that compound 1436 may have applications in the treatment of HIV and SIV. It is now shown that this compound has activity against HSV-infected lymphocytes and is proposed to also be active against human herpes virus type 6 ("HHV6"), human T-cell leukemia virus type 1 ("HTLV1"), and other viruses known to infect lymphocytes. From the activity of compound 1436, applicants also concluded that compound 1436 may be useful in treating diseases and disorders that rely on proliferation of cells, such as leukemias and other cancers. Tests relating to these anticipated properties of compound 1436 are described in more detail below.

In addition to its effects on cell proliferation, 1436 has been shown to have other useful properties. In one embodiment, 1436 is shown to have anti-arthritis activity in both a delayed hypersensitivity model and in a collagen-induced arthritis model. Compound 1436 has also been shown to have an effect on weight gain, which is caused by an effect on growth hormone production and an effect on diuresis.

This invention will be described below in terms of various specific examples and preferred embodiments. These examples and embodiments should be considered to be illustrative of the invention, and not as limiting the same.

EXAMPLE 1

Antiviral Activity of Compound 1436

A. Compound 1436 Effects on Lymphocytes

Viruses enter the human body and attach to a cell, such as a lymphocyte cell, thereby infecting the cell and recruiting it to support the growth and replication of the virus. Compound 1436 is believed to interrupt this process. The mechanism by which compound 1436 is believed to act to inhibit viral replication is described in more detail below, with reference to FIG. 3. As shown at the top portion of FIG. 3, under normal conditions (i.e., when compound 1436 is not present), the virus attaches to the lymphocyte cell, the lymphocyte cell gets infected, the sodium proton pump or the "NHE pump" is turned on and acts in a normal manner, i.e., the cell is activated and additional virus is produced (in other words, the virus replicates).

Figure 3:
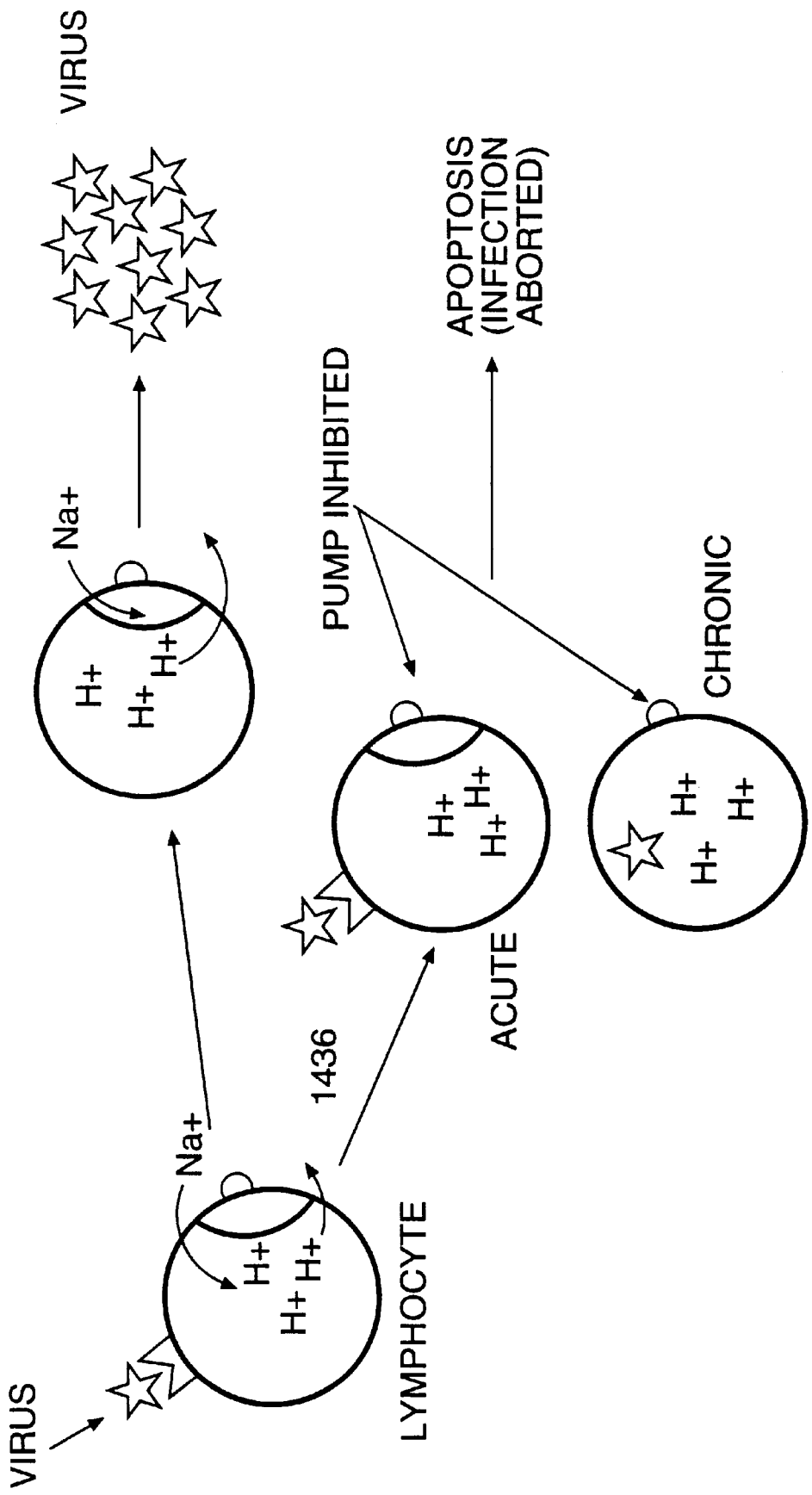
FIG. 3 is a schematic diagram illustrating a mechanism explaining the antiviral activity of compound 1436.

Applicants have discovered, however, that the presence of compound 1436 inhibits activation of at least one sodium proton antiporter isoform found in lymphocyte cells, namely NHE3. It is believed that this NHE3 inhibiting activity of compound 1436 provides a mechanism for the antiviral activity of the compound. This possible mechanism for the antiviral action of compound 1436 is illustrated toward the bottom of FIG. 3. When compound 1436 is present, the NHE pump is inhibited, and activation of the cell is stopped. Because cell activation is important for duplication or replication of infectious viral particles, such as HIV and other lymphotropic viruses, the presence of compound 1436 aborts the infection. The combination of 1436 and the foreign virus infection drives the infected cells into apoptosis (i.e., the infected lymphocyte cells die). FIG. 3 depicts the action of 1436 on both acute and chronic HIV infections.

This mechanism explains applicants' observation that compound 1436 is effective in inhibiting the growth of the AIDS virus in vitro without exhibiting cytotoxicity in vitro against human T-lymphocyte cells. In other words, the replication or duplication of HIV is inhibited and the infected cells die, but the uninfected lymphocyte cells do not die. Compound 1436 also has been found to restrain viral replication from chronically or latently infected lymphocyte cells.

Figure 4:
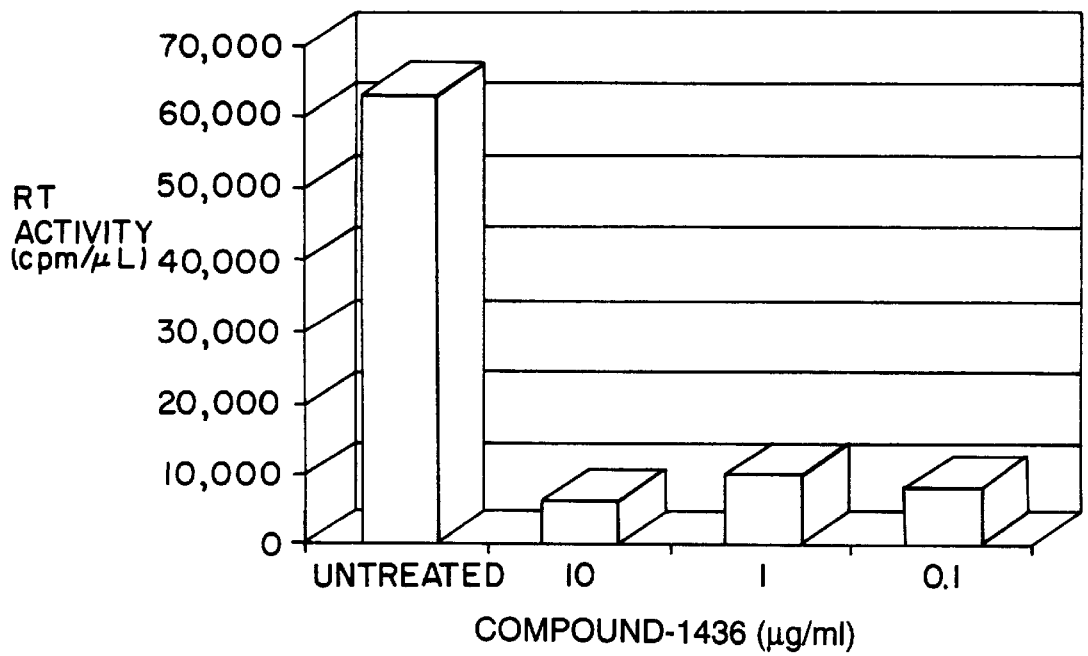
FIG. 4 shows the inhibition of HIV viral replication in an acute infection using 1436.

Various experiments were performed to test the antiviral activity of compound 1436. FIG. 4 illustrates the effect of compound 1436 on the inhibition of HIV viral replication in peripheral blood mononuclear lymphocyte cells (PBMC) that are acutely infected with a high concentration of HIV-BaL (1 viral particle: 100 lymphocytes). In this experiment, twenty units of interleukin-2 ("IL-2") were added to the tissue cultures to stimulate and promote the growth of the lymphocytes in the tissue cultures. This stimulatory material is well known to those skilled in the art. Stimulation proceeded for three days. The cells were washed, then exposed to IL-2 and 1436 in the concentrations shown in the figure. After 30–60 minutes, HIV-BaL was added. The cells were fed every 3–4 days, but no additional HIV was added. The inhibitory activity was measured on Day 7 following primary infection. As shown in the Figure, compound 1436 dramatically down regulates viral replication (measured as RT Activity (counts per minute per microliter)), even where the compound 1436 dose is as low as 0.1 $\mu$g/ml. In a related experiment, using a higher multiplicity of infection (1 viral particle: 10 lymphocytes), a 1436 dosage response was observed, e.g., the higher the compound 1436 dosage, the lower the viral replication activity (RT value).

Figure 5:
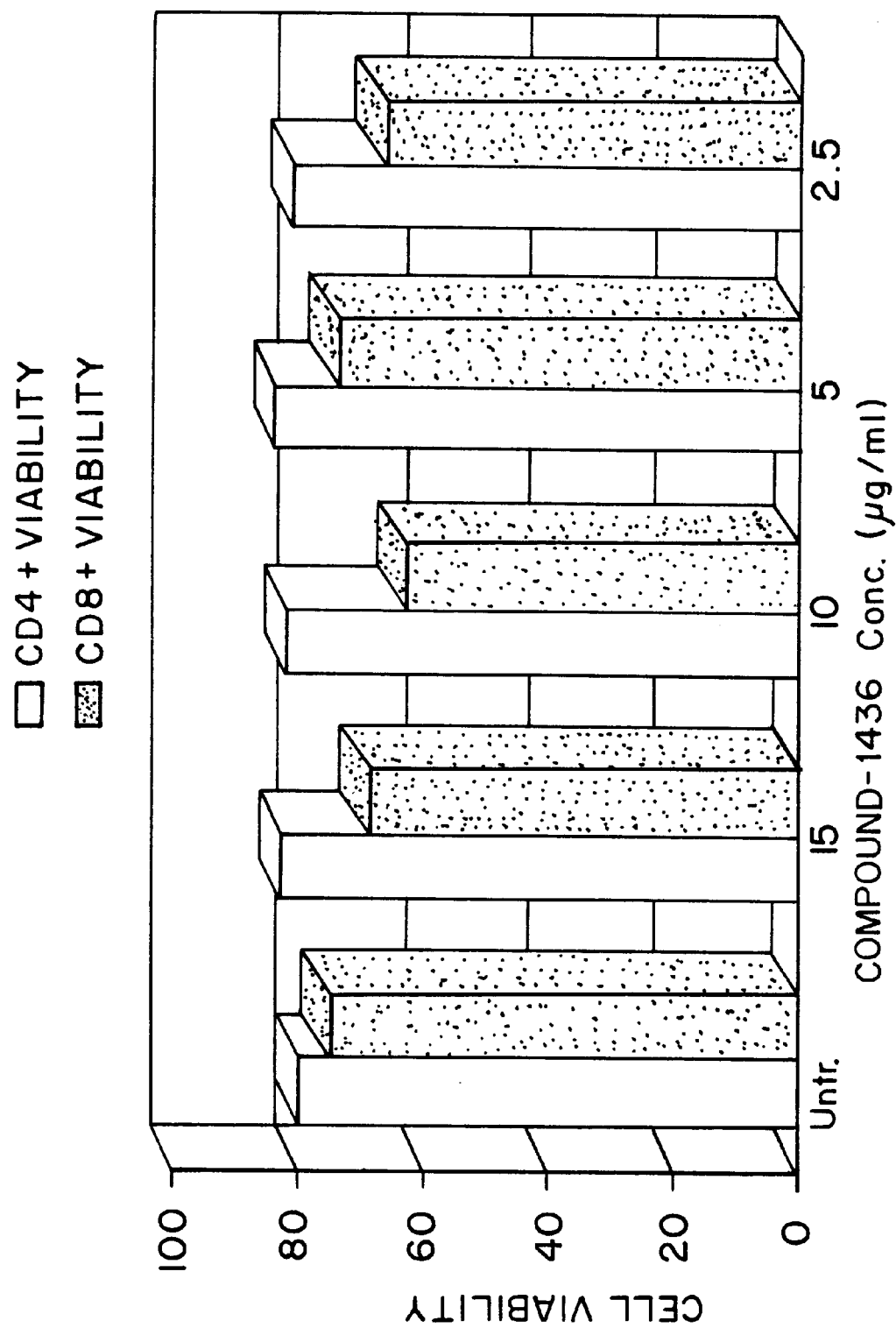
FIG. 5 graphically illustrates the effect of 1436 on lymphocyte viability at various concentrations.

Despite its antiviral activity, however, it has been demonstrated that compound 1436 does not significantly alter or effect the viability of various lymphocyte cell lines, e.g., cells bearing cell determinant 4 ("CD4+") or cells bearing cell determinant 8 ("CD8+"). Compound 1436 was added to tissue cultures including the above-noted lymphocyte cells of an uninfected individual. As shown in FIG. 5, compound 1436 had little effect on the viability of these CD4+ or CD8+ lymphocytes. This lack of difference with lymphocyte subsets was observed at several 1436 concentrations between 2.5 and 15 $\mu$g/ml. Therefore, the above noted viral inhibitory effect of compound 1436, as described in conjunction with FIG. 4, is not a lymphotoxic effect. This information supports the antiviral mechanism for compound 1436 as described above (see FIG. 3).

Figure 6:
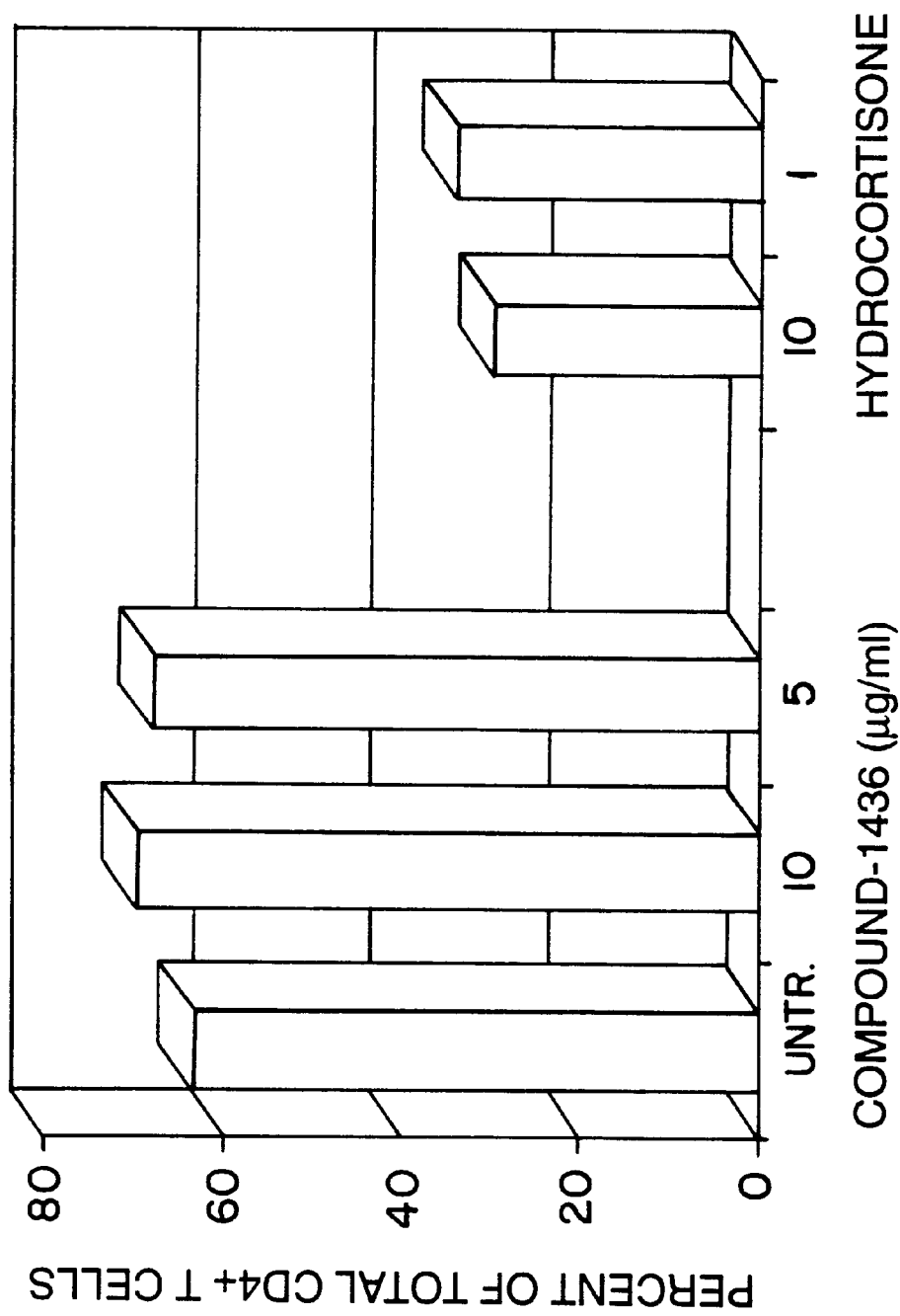
FIG. 6 graphically illustrates the effect of 1436 on HLA-Dr expression in CD4+ cells.

The experiment relating to FIG. 6 further supports the antiviral mechanism described above. FIG. 6 shows the effect on HLA-Dr expression and also shows that compound 1436 does not decrease the growth of CD4+ lymphocyte cells. The process used to obtain this data corresponded to the process described above with respect to FIG. 4. At a concentration of 10 $\mu$g/ml 1436, as compared to the untreated sample, no inhibition of the expression of HLA-Dr was found at Day 11. Hydrocortisone ("HC"), on the other hand, was shown to significantly inhibit HLA-Dr expression. Therefore, the mechanism by which compound 1436 acts is not believed to be the same as the general corticoid or steroid mechanism, as exhibited by hydrocortisone.

Figure 7A:
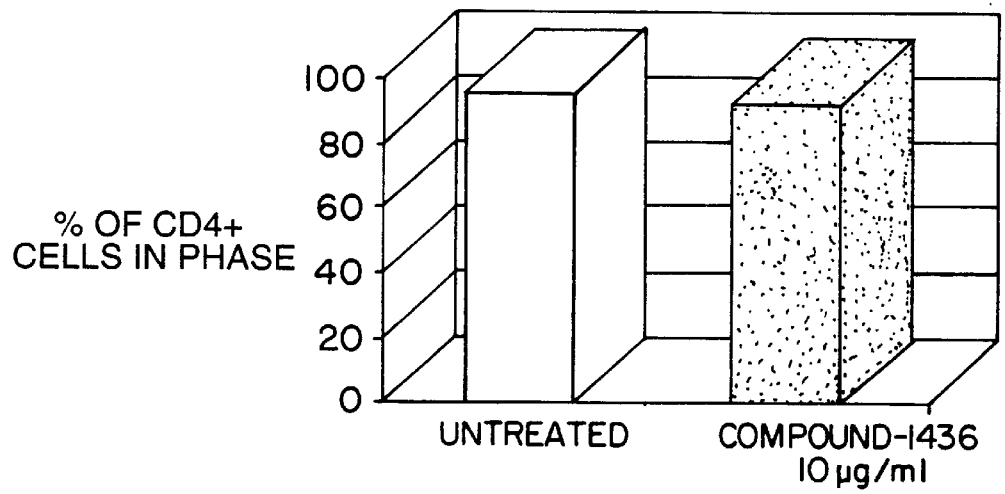
FIGS. 7a and 7b graphically illustrate that 1436 does not alter CD4+ cell cycles.
Figure 7B:
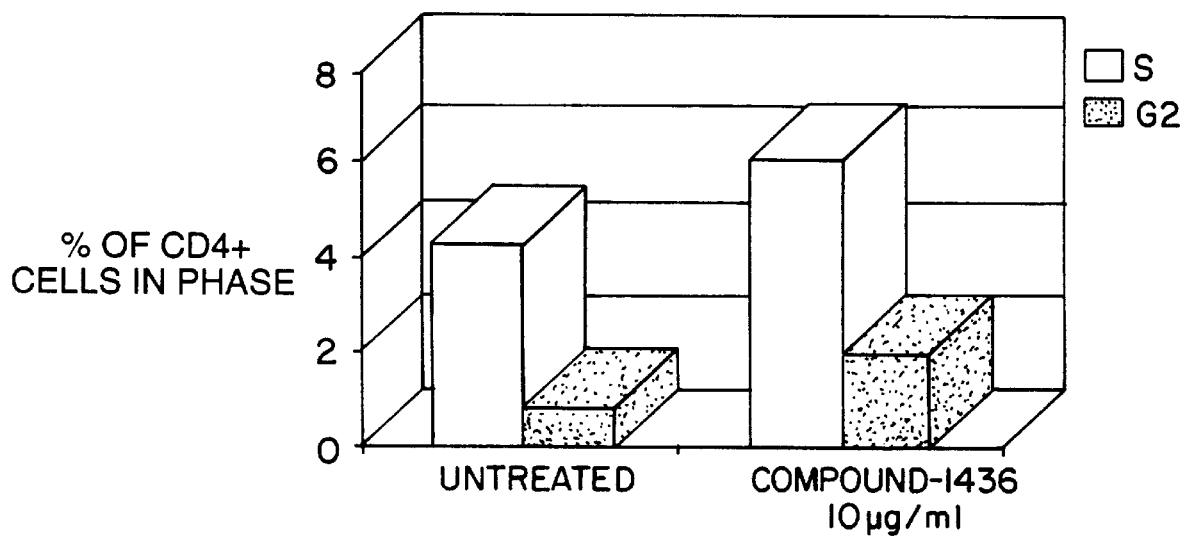

Further investigation was conducted to determine whether compound 1436 was changing the cell cycle dynamics of the lymphocyte cells. The measurement of the cell cycles is conventional and well known in this art. FIGS. 7a and 7b illustrate that the Gap 1 ("G1"), Gap 2 ("G2") and synthesis ("S") phase cycles of CD4+ lymphocyte cells are not disturbed by 1436. Only modest changes in these cell cycles were observed between CD4+ cells that were untreated and CD4+ cells that were treated with 10 $\mu$g/ml of compound 1436.

Figure 8:
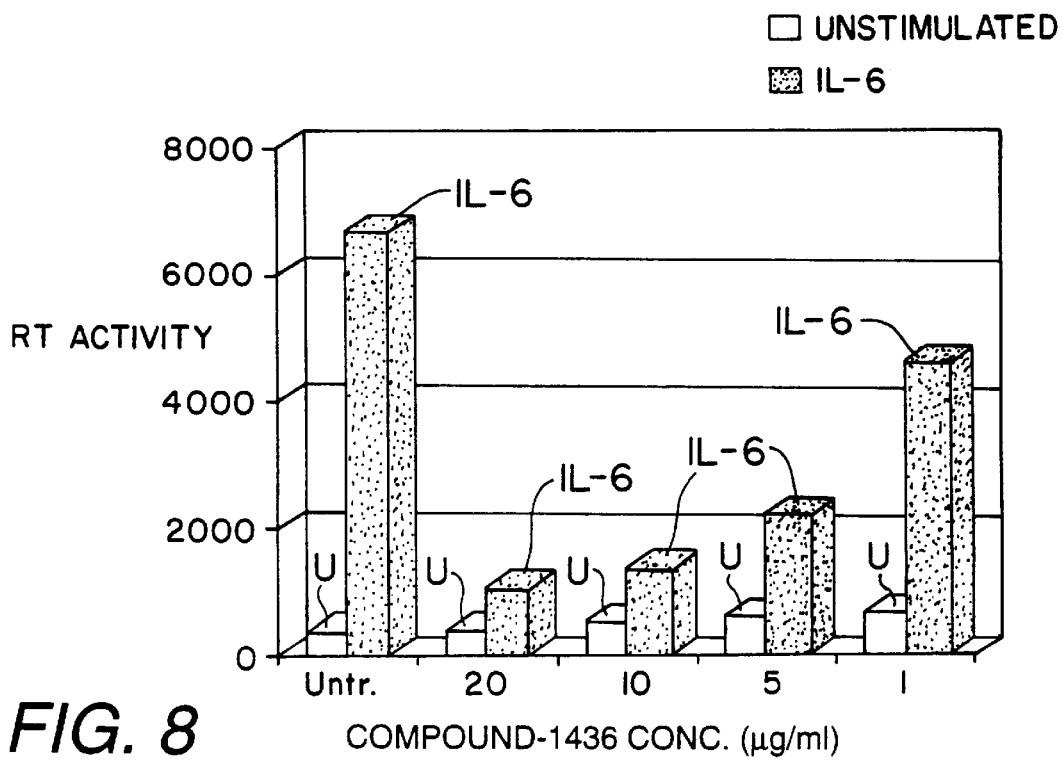
FIG. 8 shows the effect of 1436 on IL-6 stimulated human promonocytic cells chronically infected with HIV.

FIG. 8 shows the experimental results where compound 1436 was used to treat a chronically infected promonocytic cell line (U1), with and without interleukin type 6 ("IL-6") stimulation to increase viral production. Compound 1436 and IL-6 were administered together in this experiment. The stimulant IL-6 is known to those skilled in the art. Even when stimulated with IL-6, compound 1436 down regulated (i.e., suppresses) viral replication over a wide range of concentrations, even as low as 1 μg 1436/ml. The 1436 dosage response in this model also is evident from FIG. 8.

Figure 9:
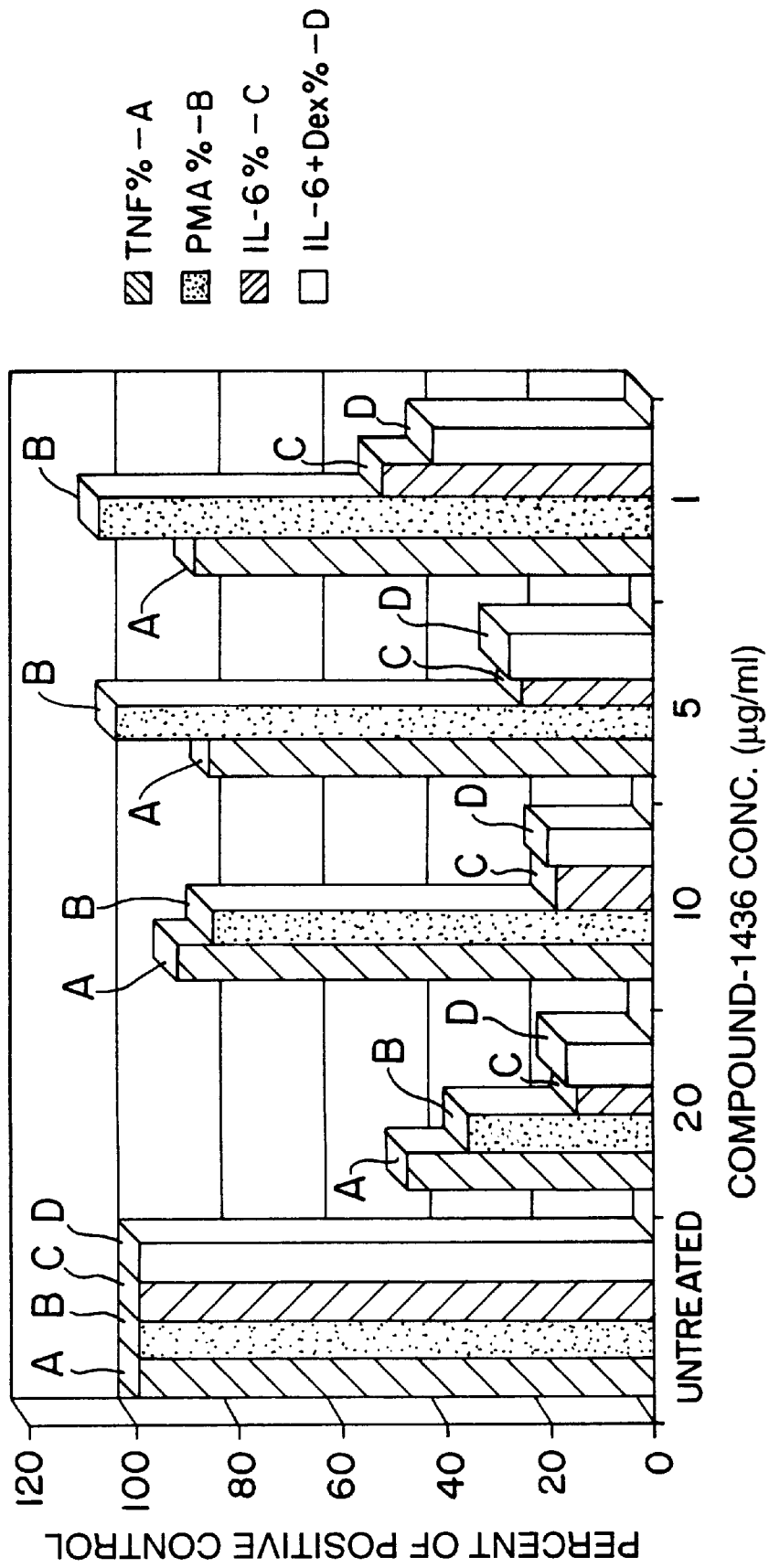
FIG. 9 shows that 1436 effects post transcriptional events during HIV infections.

Various cytokines, such as IL-2 and IL-6, described above in connection with FIGS. 4 and 8, respectively, are known to those skilled in this art. Transcriptional and post-transcriptional stimuli are known. For example, dexamethasone ("Dex") is known to synergize with IL-6 to up regulate viral replication. These are post-transcriptional stimuli, i.e., their effect occurs after RNA is transcribed. Tumor necrosis factor a ("TNFα") and the phorbol ester PMA are known transcriptional stimuli. FIG. 9 shows the effect of compound 1436 against HIV expression induced by these various stimuli (the 1436 test results are normalized against the untreated samples, as shown in FIG. 9). In these experiments, compound 1436 was administered at the same time as the stimuli. Little effect is observed when using compound 1436 to treat cells that were stimulated with the transcriptional stimuli TNFα and PMA (except at the highest 1436 concentration of 20 μg/ml). Dramatic down replication is observed, however, when 1436 was used to treat cells that were stimulated with IL-6 and the IL-6/Dexamethasone combination. Accordingly, this figure indicates that 1436 is effecting post-transcriptional events of the virus (and not actual viral transcription).

B. Compound 1436 Effects on the Herpes Simplex Virus

In addition to inhibiting HIV viral replication, compound 1436 also was found to be effective in inhibiting proliferation of the herpes simplex virus (HSV)-type 1. HSV is not a typical lymphotropic virus, but it can replicate in lymphocytes (especially in activated lymphocytes). Thus, the following tests were conducted with HSV using lymphocytes as the host cells.

Figure 10:
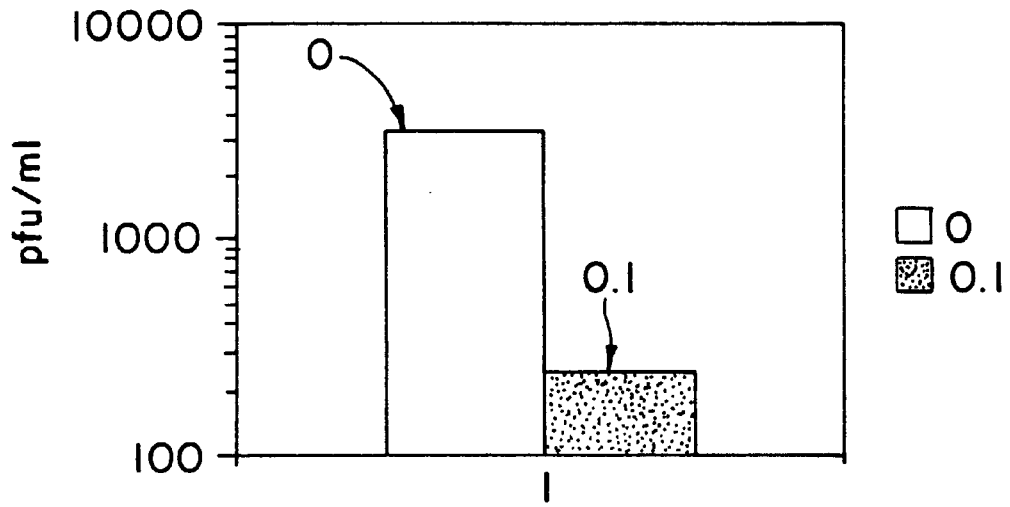
FIG. 10 shows that 1436 inhibits the replication of herpes simplex virus at low multiplicity of infection (MOI)
Figure 11:
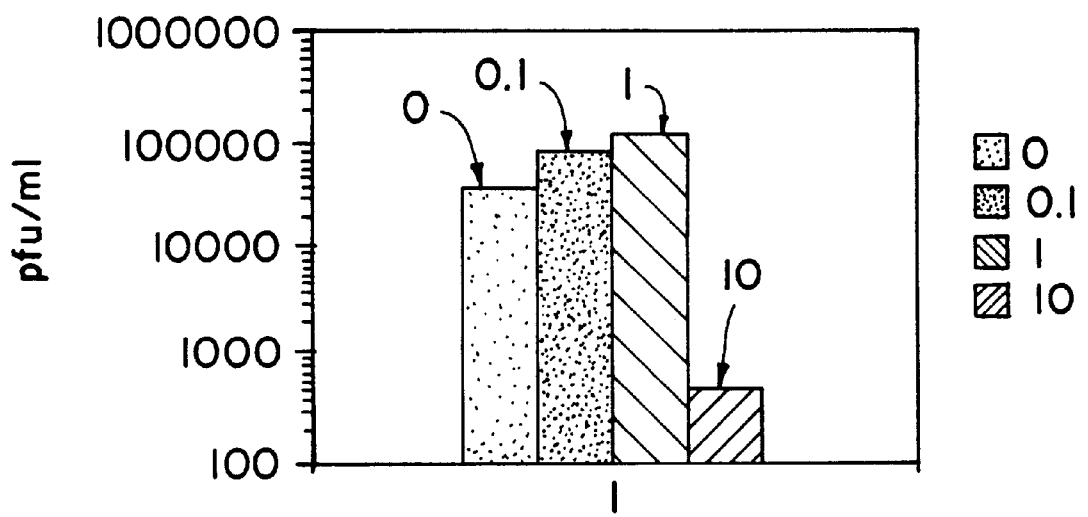
FIG. 11 shows that higher doses of 1436 inhibit the replication of herpes simplex virus at high MOI.

For the test of FIG. 10, primary T lymphocyte cells were subjected to a pre-treatment with compound 1436 at a dosage of 0.1 μg/ml. Twenty-four hours after the 1436 pre-treatment, the 1436 treated T-cells then were exposed to HSV. As shown in FIG. 10, 0.1 μg 1436 per milliliter was effective in inhibiting replication of the HSV virus in primary T-type lymphocyte cells. In this case, the cells were infected with HSV at a low multiplicity of infection ("MOI") (e.g., about 0.05 plaque forming units per milliliter (~0.05 pfu/ml)). In a related experiment, a 10 μg/ml 1436 pre-treatment was needed to produce a significant inhibitory effect when the T cells were infected with HSV at a high MOI (about 5 pfu/cell). See FIG. 11. Co-treatment of compound 1436 with the HSV exhibited little effect against HSV at any dosage and at any MOI level tested. Additionally, when compound 1436 was added as a post-treatment after infection with the HSV virus, little inhibitory effect was observed.

Figure 12:
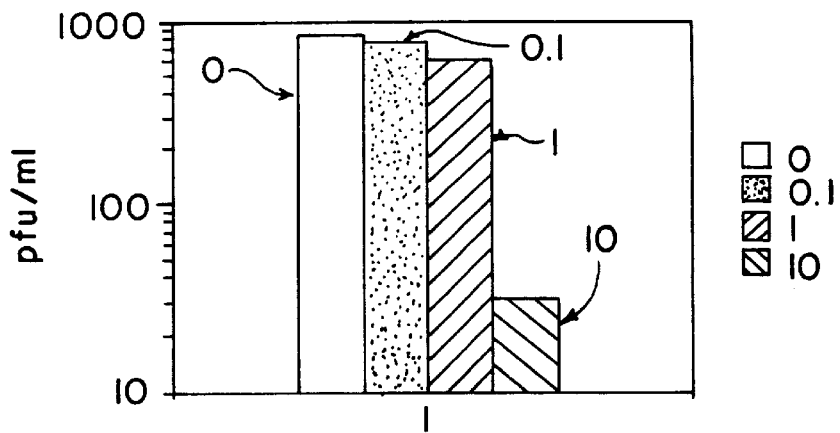
FIG. 12 shows that 1436 can inhibit the replication of herpes simplex virus in a T-lymphoma cell line.

HSV growth in an A3.01 CD4+ T-lymphoma cell line was inhibited by a 10 μg/ml pre-treatment treatment dosage of compound 1436, as illustrated in FIG. 12 (a low MOI of about 0.05 pfu/ml was used). In this experiment, the 1436 pre-treatment was 24 hours before the exposure to HSV. In a co-treatment regimen or when using a high MOI (about 5 pfu/cell), however, compound 1436 had little inhibitory effect on HSV replication.

Based on the information and data gathered from this test, it was concluded that HSV infection in primary lymphocytes can be inhibited with 1436 treatment, particularly where 1436 is used as a pre-treatment (i.e., in a treatment before exposing the cell to the virus). In addition, it was concluded from this series of experiments that the effects of 1436 are specific for the host cell, i.e., here, the primary T lymphocyte, rather than specific for a given virus. Notably, HIV is a retrovirus (single-stranded RNA genome), while herpes simplex virus is a double stranded DNA virus. Compound 1436 has been found to inhibit replication of both of these viral strains.

EXAMPLE 2

Anti-Cancer Activity of Compound 1436

Like viral diseases, cancerous tumors depend on cell division and proliferation to grow and spread. Because of its effects on inhibiting cell proliferation, applicants believed compound 1436 to be a candidate in treating various cancerous conditions, such as melanoma and leukemias. The following tests describe efforts made to test the effectiveness of compound 1436 against various cancers.

A. Compound 1436 Effects Against Melanoma

Figure 13:
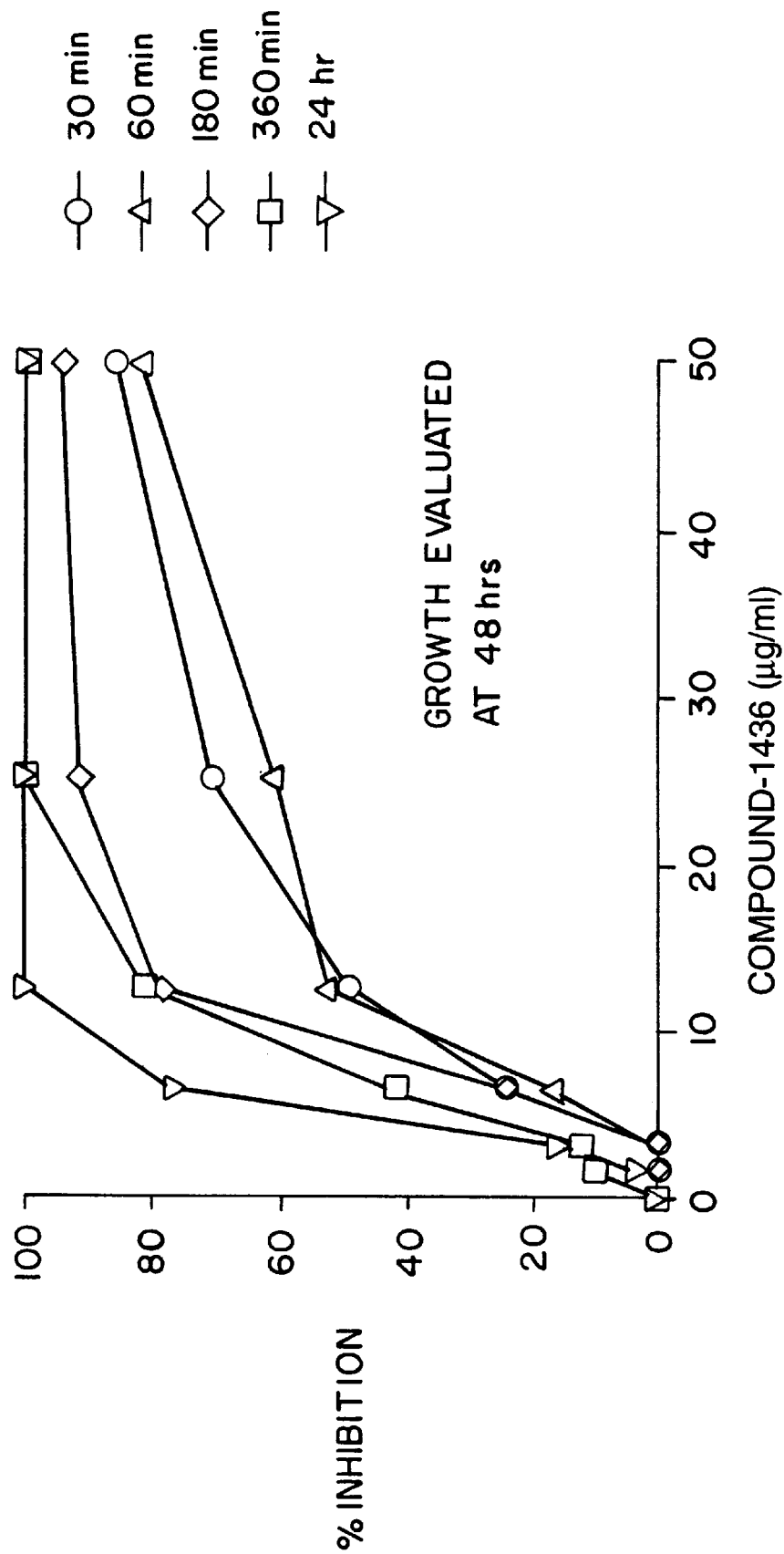
FIG. 13 illustrates the effect of 1436 exposure time on human melanoma cells.

The effect of exposure of human melanoma cells to compound 1436 was tested, and the test results are shown graphically in FIG. 13. Melanoma cells were exposed to 1436 at various concentrations for time periods between 30 minutes and 24 hours. Thereafter, the 1436 was removed and the percentage of surviving or active cells was measured forty-eight hours after the experiment started. The inverse of this measurement is shown graphically in FIG. 13 as percent inhibition of cell growth. As shown in the Figure, even after short 1436 exposure times (30–60 minutes), about 50% inhibition occurred at concentrations as low as about 12 μg/ml. After a 3 hour 1436 exposure or a 6 hour 1436 exposure, about 80% inhibition occurred at concentrations of about 12 μg/ml. After 24 hours of exposure to 1436, about 80% inhibition was observed at concentrations as low as 7 μg/ml, and essentially 100% inhibition occurred at 1436 concentrations of 12 μg/ml and above. The data from this test illustrate that the inhibitory effect of compound 1436 against melanomas, while not instantaneous, is induced quite rapidly.

B. Compound 1436 Effects Against Leukemias

Figure 14:
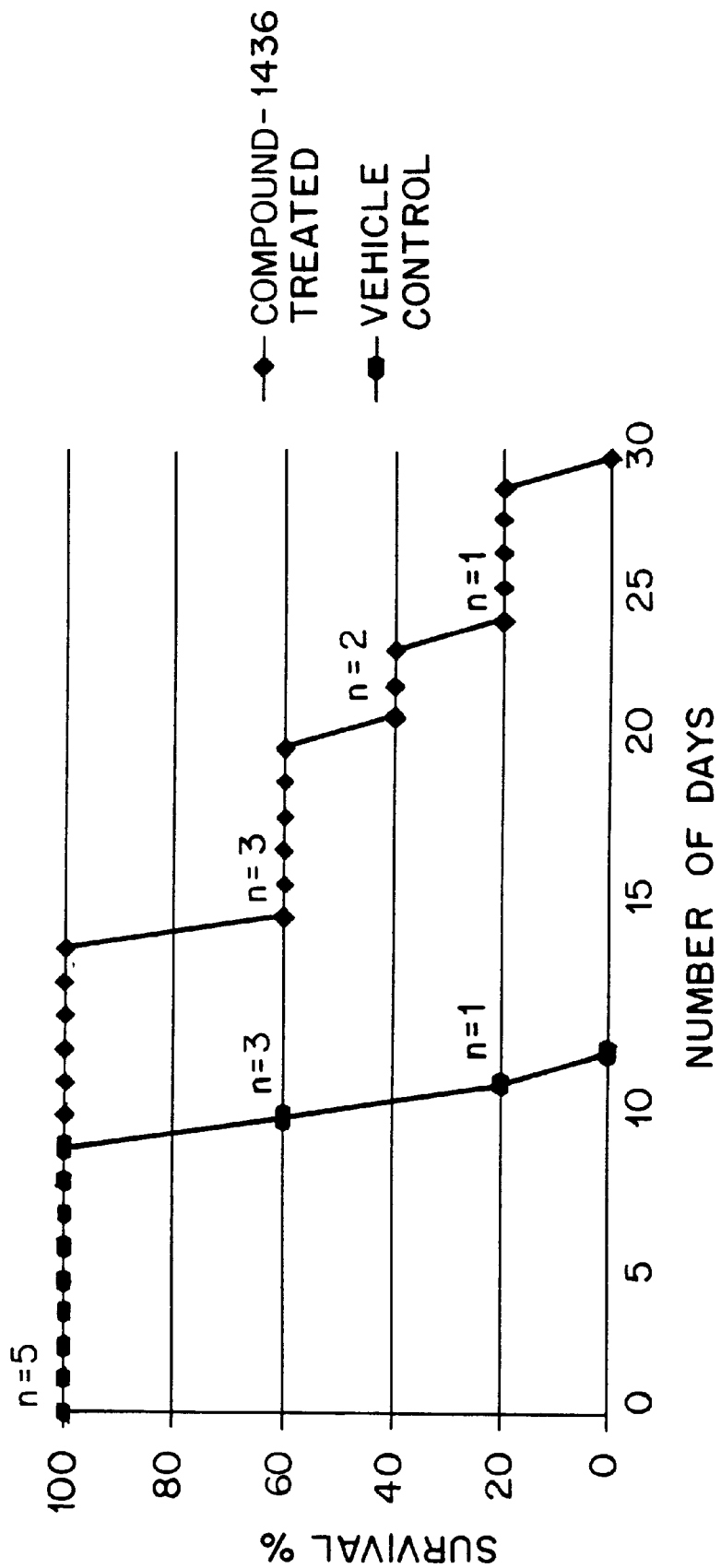
FIG. 14 shows the improved survival rate induced by treatment with 1436 in a mouse model of murine acute lymphocytic leukemia (ALL)

Compound 1436 also has been found to be effective in animal models that test for activity against both adult forms of leukemia, namely, ALL (acute lymphocytic leukemia) and AML (acute myelocytic leukemia). FIG. 14 shows the survival test results when using 1436 as a treatment against murine ALL. Mice implanted with syngeneic murine ALL were dosed at 10 mg/kg 1436 (i.p.) every third day. The control mice (treated with the carrier vehicle only) quickly succumbed to the leukemia, as evidenced by the rapid death rate for the control group after Day 9. The 1436 treated mice had a dramatically increased survival rate as compared to the control mice, as is evident from FIG. 14.

Figure 15:
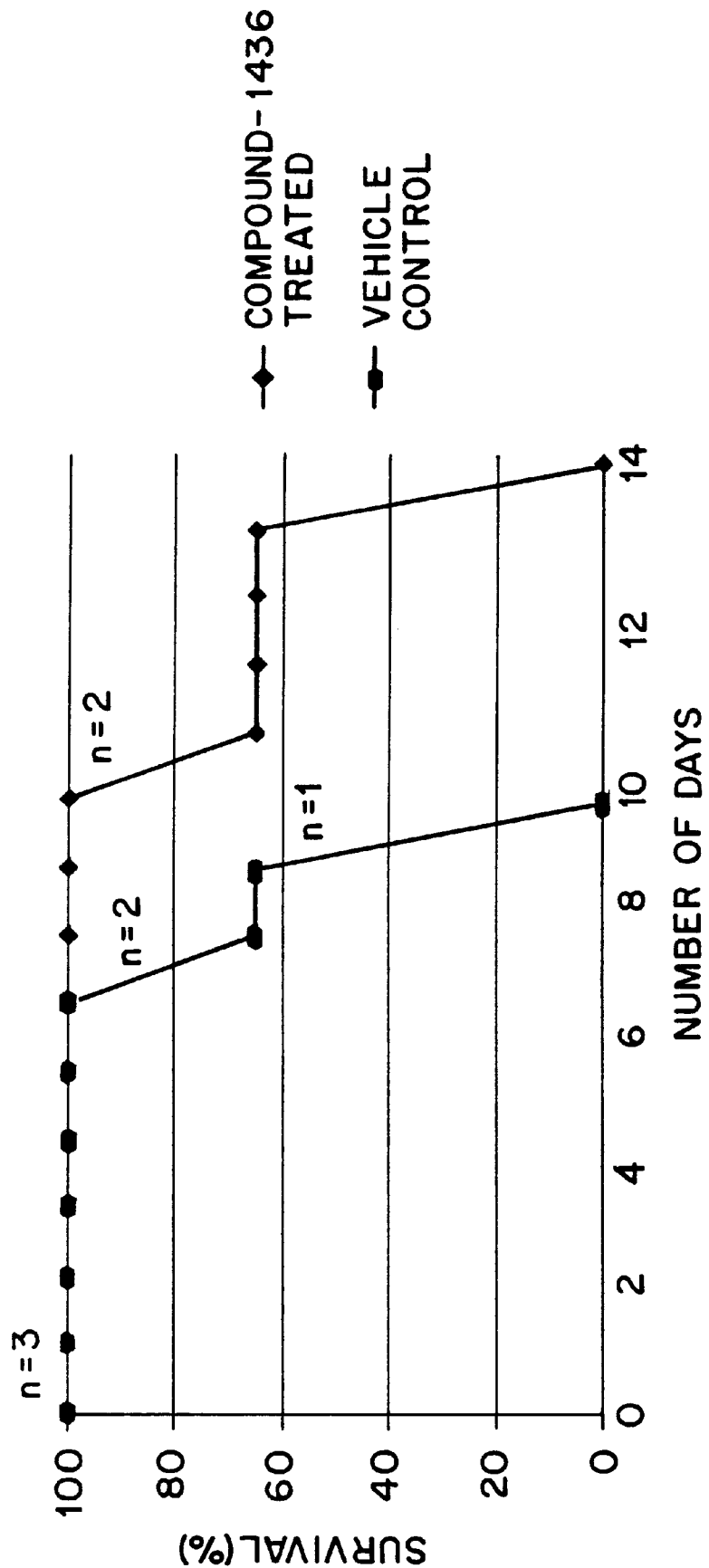
FIG. 15 shows the improved survival rate induced by treatment with 1436 in a mouse xenograft model with human myeloid leukemic cells.

Another animal model was used to test the efficacy of compound 1436 in treating AML. Severely compromised immunodeficient ("SCID") mice were injected with U97, a human myeloid leukemia cell line. As described in the previous experiment relating to FIG. 14, the 1436 treatment regimen included dosing the mice in this experiment with 10 mg/kg 1436 (i.p.) every third day. After Day 6, the control mice quickly succumbed to the leukemia (FIG. 15). The 1436 treated mice, on the other hand, showed a significantly increased survival.

EXAMPLE 3

Anti-Arthritis Activity of Compound 1436

Arthritis is an autoimmune response, where the tissues of an individual become inflamed and cause pain to the individual. Applicants tested compound 1436 in various animal models for determining its efficacy as an arthritis treatment. In the following model, the effect of compound 1436 on delayed type hypersensitivity (DTH) in mice was tested as a measure of compound 1436's usefulness in treating arthritis.

A. Delayed Type Hypersensitivity Model

To test the activity of 1436 against DTH, mice were injected on Day 0 with 250 μg of methylated bovine serum albumin (mBSA) emulsified in complete Freund's adjuvant. Eight days later, one paw of each mouse was injected with a challenge dose of 100 μg mBSA in saline. The other paw of the mouse was injected with saline only. In this way, each mouse included one test paw and one control paw. One and two days after the challenge mBSA dose, the paws were measured. If the mouse has delayed type hypersensitivity, then the paw injected with the challenge dose of mBSA swells. The differences between the paw sizes (in mm) on the mice were scored as follows: mBSA paw-saline control paw.

Figure 16:
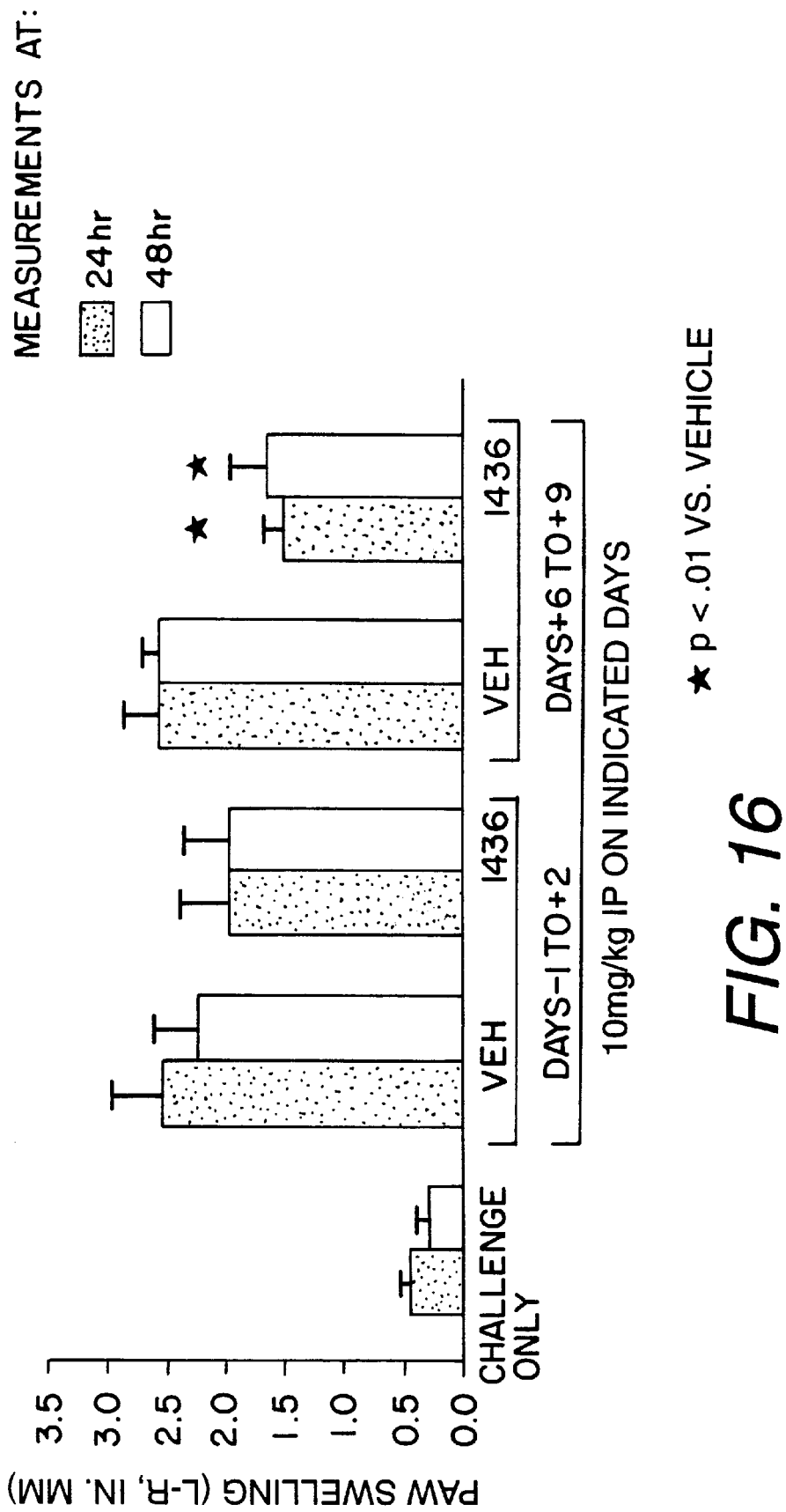
FIG. 16 illustrates the inhibitory effect of compound 1436 on paw swelling in a delayed type hypersensitive study in mice.

For the experimental test, compound 1436 was administered either at the time of the initial mBSA injection or at the time of the mBSA challenge injection. FIG. 16 shows the test results where compound 1436 was given at a daily dosage of 10 mg/kg i.p. on either (a) Days −1 to +2 (at the time of the initial mBSA injection) or (b) on Days +6 to +9 (at the time of the mBSA challenge injection). When 1436 was given during the time of the initial mBSA injection, it did not significantly interfere with or inhibit delayed type hypersensitivity. However, when compound 1436 was given over the time of the challenge mBSA dose, a reduction in paw swelling was observed.

Figure 17:
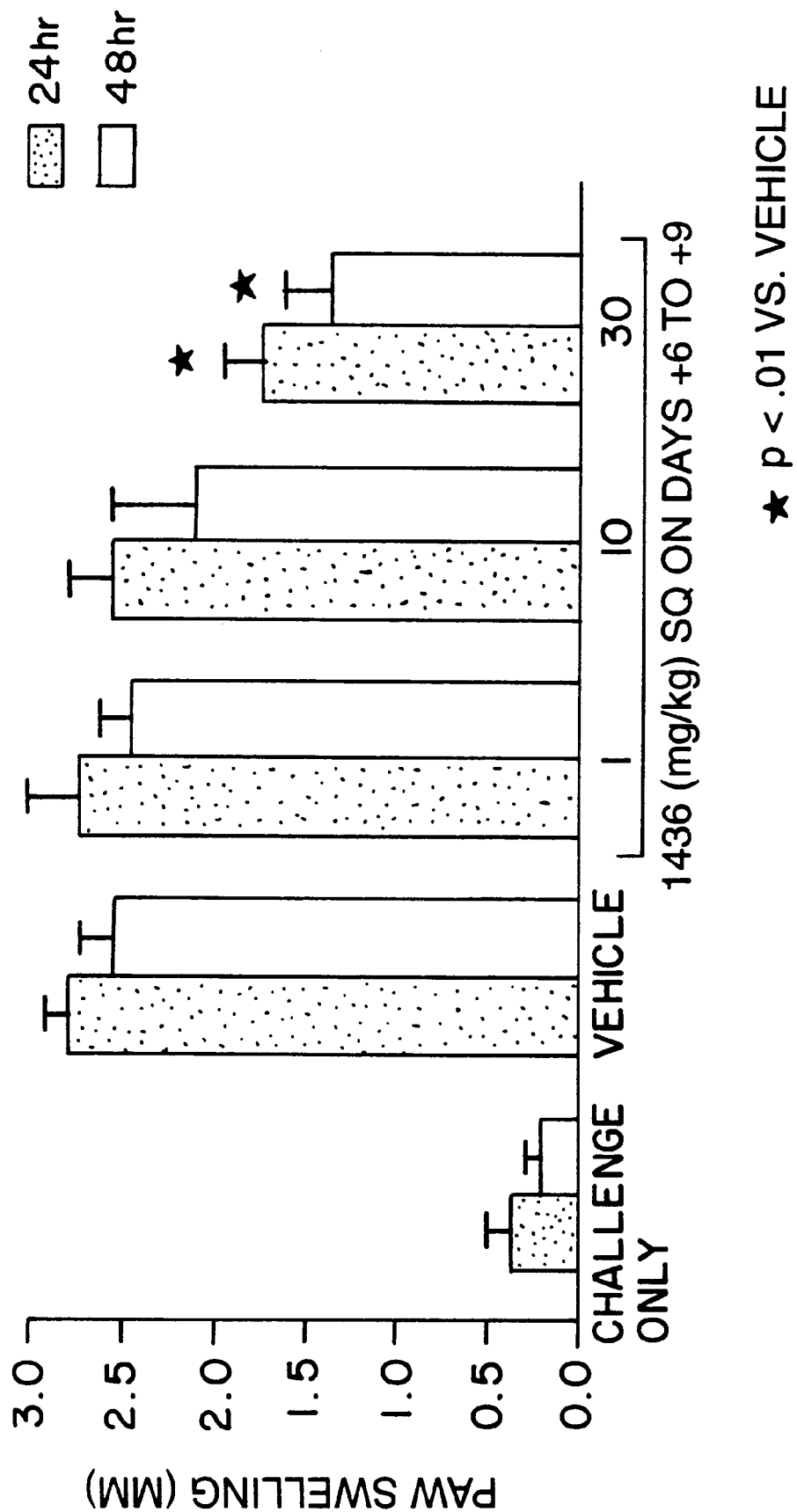
FIG. 17 also illustrates the effect of 1436 on mouse paw swelling.

In a related experiment using the same general experimental procedure described above, compound 1436 was given subcutaneously at dosages of 1, 10 and 30 mg/kg on Days +6 to +9, during the time period when the challenge mBSA dose was administered. Paw swelling was measured at 24 and 48 hours after the 1436 dose. At a dose of 30 mg/kg 1436, as illustrated in FIG. 17, paw swelling was significantly reduced. This data indicate 1436 reduces delayed type hypersensitivity at this dose.

B. Collagen Induced Arthritis Model

A second animal model for testing the effectiveness of a compound against arthritis is the bovine type II collagen induced arthritis ("CIA") or the immune-mediated arthritis model in mice. Compound 1436 also was tested in this model. Six to eight week old mice (male DBA/1LacJ from Jackson Labs) were separated into groups of 10. On Day 0, these mice were immunized subcutaneously with 100 μg of bovine articular cartilage-derived type II collagen in an adjuvant system (RIBI Immunochem.). A booster injection of collagen in RIBI adjuvant was given on Day 21.

Control groups were injected with either mouse serum albumin in phosphate buffered saline (MSA/PBS) or dexamethasone-21-phosphate ("Dex," available from Sigma) in sterile, endotoxin-screened dH$_2$O five times per week (Monday to Friday). Dexamethasone is a commercially available composition that is used to treat various swelling disorders, and it is used as a positive control in this experiment. Dex was injected at a dose of 20 μg/mouse (~1 mg/kg). Mice treated with 1436 received their first dose on Day 17, four days prior to the collagen booster. Compound 1436 was dissolved in sterile, endotoxin-screened dH$_2$O and administered subcutaneously at 200 μg/mouse (~10 mg/kg). Dosing with 1436 was continued every fourth day (10 mg/kg) for the duration of the study.

Visual assessments of paw and digit swelling and inflammation were performed three times per week (on Monday, Wednesday and Friday), and each paw was graded on the following scale (with a maximum possible score of +3 points per paw and +12 points for each mouse):

| Grade | Meaning |
| --- | --- |
| +1 | Swelling or inflammation (i.e., redness) of one or more digits/joints |
| +2 | Swelling or inflammation involving the majority of the plantar surface of the paw |
| +3 | Ankylosis or significantly compromised range of motion of the ankle/wrist joint upon flexion/extension |

At the conclusion of the study, the hind paws were severed at the hair line, above the ankle, and the paws were individually weighed.

Figure 18:
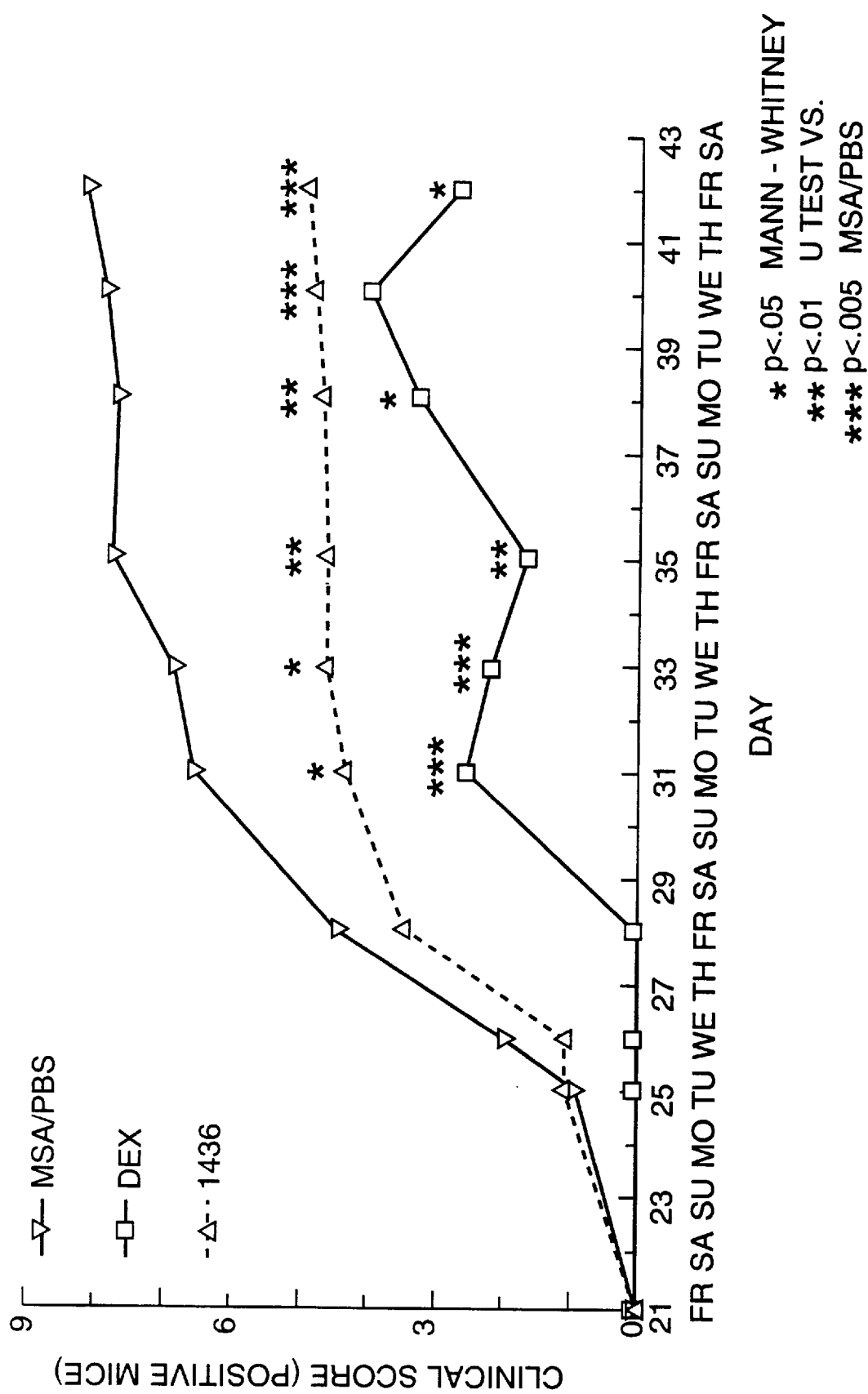
FIG. 18 shows reduced arthritic severity in 1436-treated animals in an arthritis treatment procedure.

In FIGS. 18 and 19, the test results (given as mean values) for the various groups are depicted in the graphs, and the error bars (where shown) indicate the standard deviation. Differences in the incidence of arthritis between the groups were analyzed by Fisher's exact test. Analysis of variance (ANOVA) with Dunnett's modification for multiple comparisons was used for examining differences in paw weight. A non-parametric analysis, the Mann-Whitney U test, was used to compare the arthritis clinical severity scores only for those mice that developed arthritis. Disease free mice were not included in this comparison to avoid skewing the test results. The inclusion of disease free mice in the test results makes it difficult to evaluate the severity of joint inflammation in the animals that do develop arthritis. Differences were considered significant at $p<0.05$.

FIG. 18 shows the average clinical score for each group of mice. For each mouse in the group, the grades are added together for the four paws on the animal, based on the grading system described above. This grading system provides a measure of the overall severity of the arthritis in the animal. The average overall grade for the animals in each group is provided in FIG. 18 as the average clinical score. By Day 31, all of the animals in the MSA/PBS group and the 1436 treated group had developed arthritis. Disease severity reached a plateau in the MSA/PBS group by about Day 35 (at a mean aggregate clinical score per mouse of about 8). A similar plateau was observed for the 1436 treated mice by Day 33–35, but the degree of inflammation in the 1436 treated group was significantly lower, and the clinical score of the 1436 treated mice (a mean aggregate score of about 5) was significantly lower than the clinical score of the MSA/PBS control group.

The use of Dex markedly reduced the degree of inflammation in arthritic mice. As shown in FIG. 18, however, significant fluctuations in the arthritic severity (and clinical score) were observed, coinciding with the on-off/week-weekend dosing regimen used with the Dex.

FIG. 19 illustrates that the inflammation in the arthritic paws was accompanied by edema and a resulting increase in paw weight. The hind paws were weighed at the termination of the study (Day 42). Compared to the inflamed paws from the MSA/PBS treated mice, paws from the mice treated with either Dex or compound 1436 were significantly lower in weight, reflecting the milder inflammation and arthritic severity in these groups. As shown in FIG. 19, the paw weights of the Dex and 1436 treated groups were not significantly different from that of a group of mice treated with 1436 alone without the collagen booster at Day 21.

Based on the information derived from these tests as described in connection with FIGS. 18 and 19, it was concluded that compound 1436 is effective as a prophylactic treatment for arthritis. While the overall incidence of the disease was not altered by 1436 as compared to the MSA/PBS control group, the severity of swelling and degree of joint involvement was significantly attenuated by compound 1436. The anti-inflammatory activity of compound 1436 also is apparent from the test results described above in conjunction with FIGS. 18 and 19.

EXAMPLE 4

Body Weight Effect of Compound 1436

Tests were conducted on compound 1436 to determine the effect of its administration on the body weight of mammals.

In the procedure for the Collagen Induced Arthritis Model described above, an additional group of immunized mice (including 5 mice) was dosed with compound 1436 in the same manner and by the same regimen as the other 1436 treated animals. This additional group of mice was treated in this manner for the purpose of observing the weight-modulating effect of compound 1436. On Day 0, the mice of this additional group were immunized subcutaneously with 100 μg bovine articular cartilage-derived type II collagen in an RIBI adjuvant system. This additional group of 1436 treated mice, however, did not receive a collagen booster at Day 21. Like the other group of 1436 treated mice, these mice received their first 1436 dose on Day 17. Compound 1436 was dissolved in sterile, endotoxin-screened dH$_2$O and administered subcutaneously at 200 μg/mouse (~10 mg/kg). Dosing with 1436 was continued every fourth day (10 mg/kg) for the duration of the study. The mice were weighed approximately weekly on the days indicated in FIG. 20.

Between Day 25 and Day 32, mice in the MSA/PBS control group lost about 15% of their body weight, coinciding with the onset and progression of arthritis. See FIG. 20. A similar weight loss was observed in the 1436 treated mice, irrespective of whether the mice received the collagen booster injection at Day 21, and despite the fact that the 1436 treated mice were relatively disease free. While the body weight of the MSA/PBS mice remained relatively constant after Day 32, the body weights of the 1436 treated mice (with and without the collagen booster) continued to decline through Day 39. Thus, this study indicates that 1436 may be useful to regulate weight gain. The Dex treated mice showed a stable weight pattern over the entire course of the study period.

In the Collagen Induced Arthritis Model described above, two of the five mice in the additional 1436 control group developed mild arthritis (clinical score of 2) despite having received no collagen booster immunization at Day 21. It was noted, however, that these mice received the priming collagen immunization at Day 0. This priming collagen injection is sufficient to induce arthritis in some animals.

Figure 21:
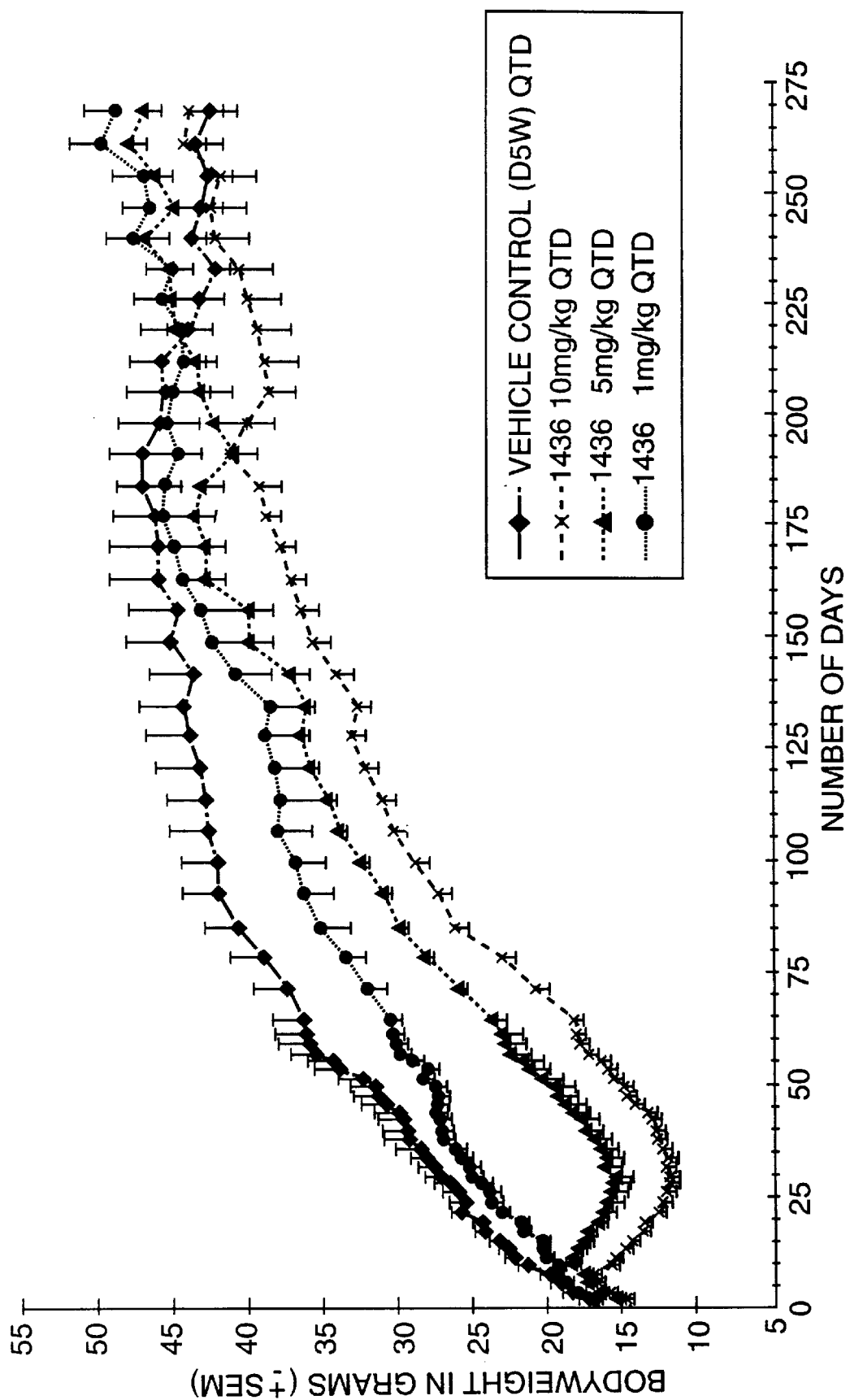
FIG. 21 shows the effect of 1436 on the body weight of mice in a dose response study.

Additional testing was performed to demonstrate the effect of compound 1436 on the body weight of mice. The dosage effect of compound 1436 was tested in one experiment. As illustrated in FIG. 21, compound 1436 was administered subcutaneously into BDF1 male mice in dosages of 1, 5 and 10 mg 1436/kg body weight every third day ("QTD") from Day 1 to Day 22. The control vehicle and the 1436 administration vehicle in this experiment was 5% Dex in water. At 5 and 10 mg/kg 1436, weight gain was suppressed in these groups, and in fact, significant weight loss was experienced. Note the surprising decrease in the body weight of the mice treated with these doses of compound 1436. While these 1436 treated animals experienced a significant weight loss, however, they did not slow down and become lethargic. Rather, they were normally active and apparently healthy. 1 mg/kg 1436 did not appear to have a significant effect on the body weight of the mice in that group. Notably, after the 1436 treatment was stopped (at Day 22), weight gain returned in the animals treated with the 5 and 10 mg 1436/kg body weight doses. Eventually, after 1436 treatment was discontinued, the body weight of the animals in these groups reached the level of the animals in the other groups.

Figure 22:
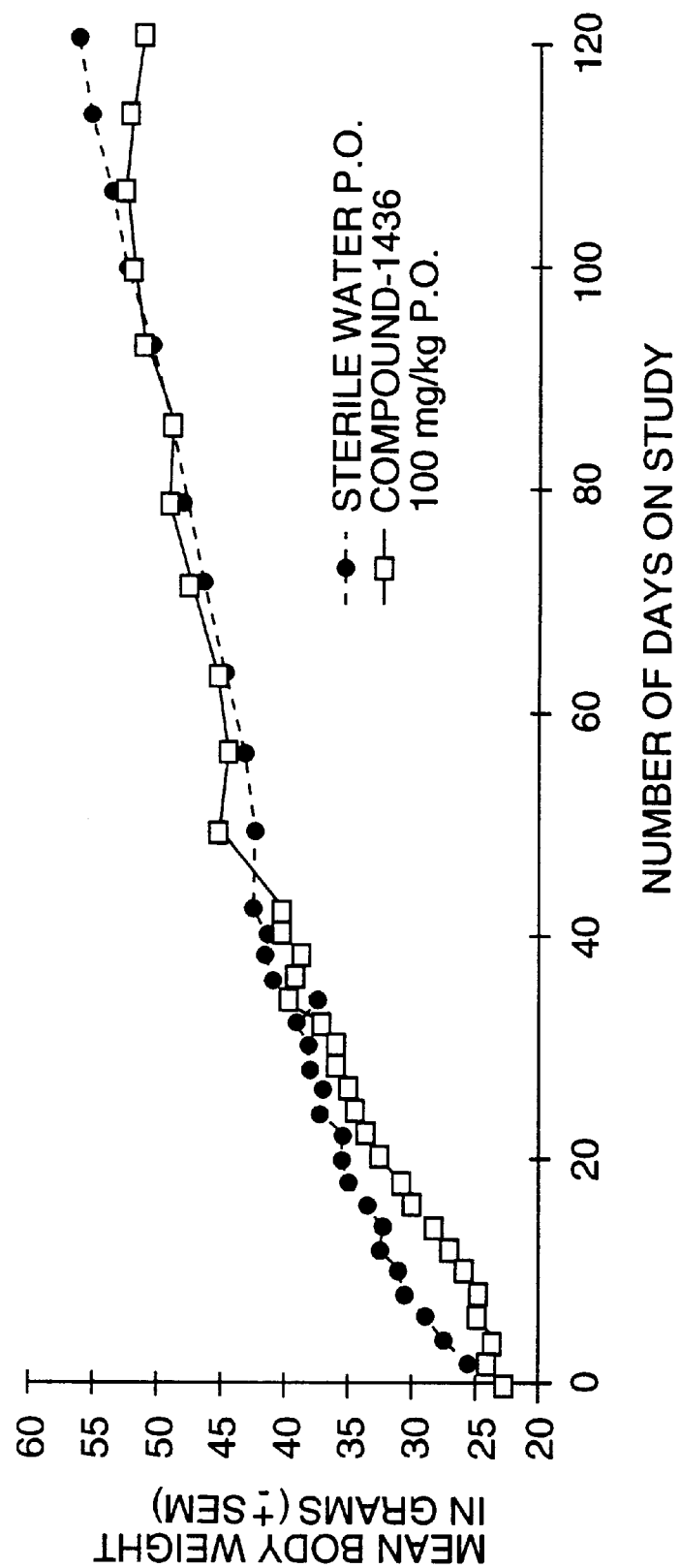
FIG. 22 shows the effect of oral dosing of 1436 on the body weight of mice.

For oral dosing of compound 1436, as shown in FIG. 22, about 60 mg/kg active agent induced a weight suppression effect, which was most obvious on day 10 of the study. In this experiment, the CD-1 male mice were dosed orally with 60 mg/kg active once every third day (QTD) on days 0, 3 and 6, with a dosage volume of 0.01 ml/g. Note that 100 mg/kg 1436 is approximately equivalent to 60 mg/kg active. Again, after 1436 treatment was stopped, the body weight of the 1436 treated animals returned to the level of the animals in the control group.

Figure 23:
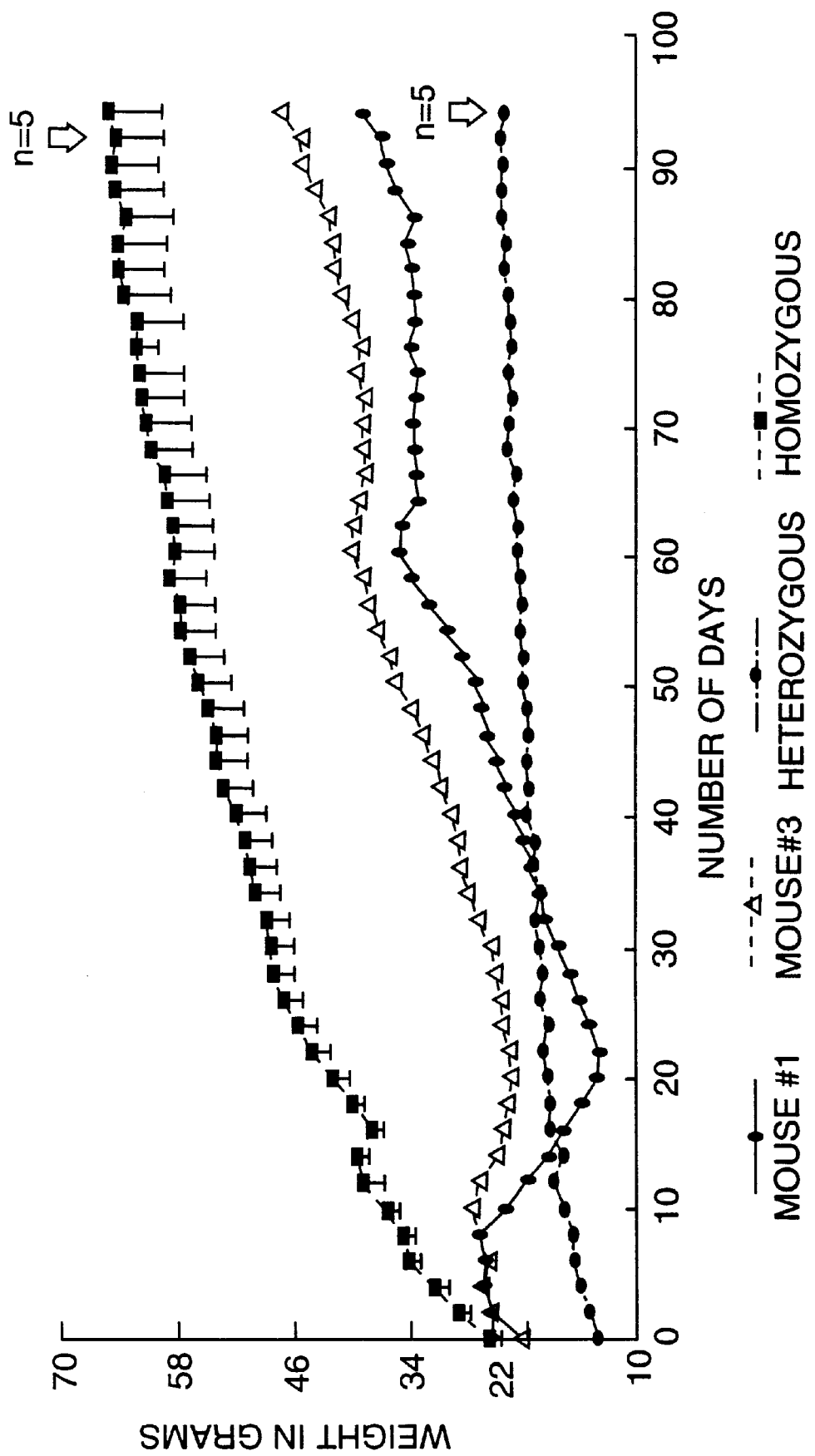
FIG. 23 shows the effect of 1436 on the body weight of obese mice (OB/OB)
Figure 24:
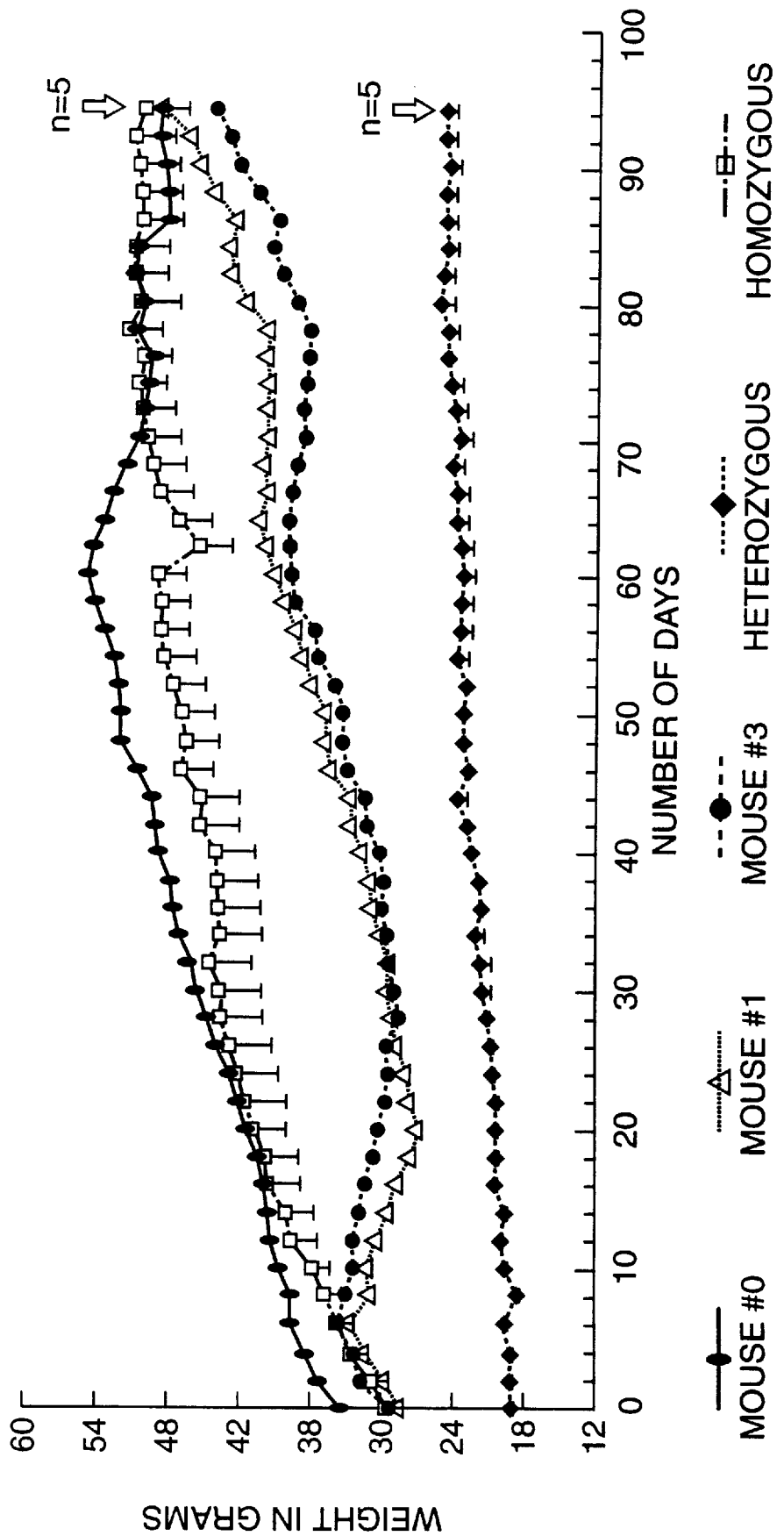
FIG. 24 shows the effect of 1436 on the body weight of diabetic mice (db/db)

In another experiment, genetically obese mice (OB/OB) and diabetic (db/db) mice were treated with compound 1436 to determine the effect on their body weight. Both homozygous (n=5) and heterozygous (n=5) control mice for both OB/OB and db/db mice were treated with sterile H$_2$O (vehicle). The test results are illustrated in FIGS. 23 and 24. Weight loss and weight control were achieved for the 1436 treated mice. FIGS. 23 and 24 show the effects of compound 1436 (administered s.c. at a dose of 10 mg/kg on days 0, 3 and 6 and 60) on weight in OB/OB and db/db mice, respectively. In FIGS. 23 and 24, "OB/OB" and "db/db" relate to the leptin/leptin receptor.

Figure 25:
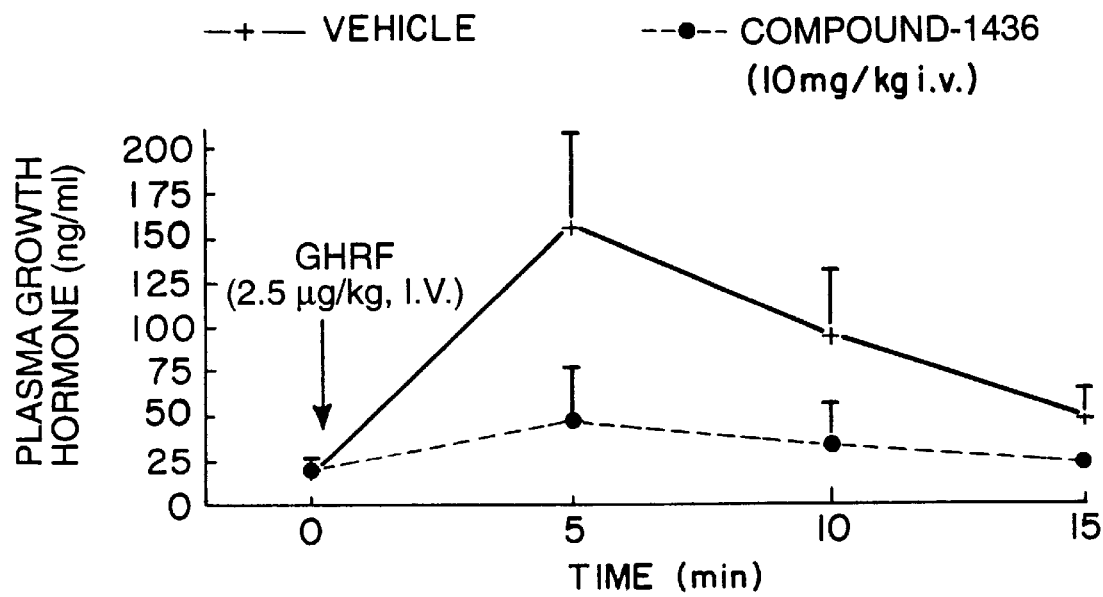
FIG. 25 shows that 1436 inhibits the action of growth hormone releasing factor (GHRF)

The body weight suppression effect of compound 1436 may be the result of suppression of growth factor production and/or growth factor release in the treated animals. To test this possibility, the effect of compound 1436 on release of growth hormone during a GHRF stimulatory test was studied. Compound 1436 or saline (vehicle) was administered at 10 mg/kg i.v. to rats 30 minutes prior to a growth hormone releasing factor (GHRF) challenge (2.5 μg GHRF/kg, i.v. at t=0), and the plasma growth hormone output was measured. Blood samples were taken at t=0, 5, 10 and 15 minutes. As illustrated in FIG. 25, compound 1436 was found to inhibit growth hormone secretion in rats during a GHRF provocation test. In this test, the GHRF is added in this system to induce an increase in growth hormone release.

Figure 26:
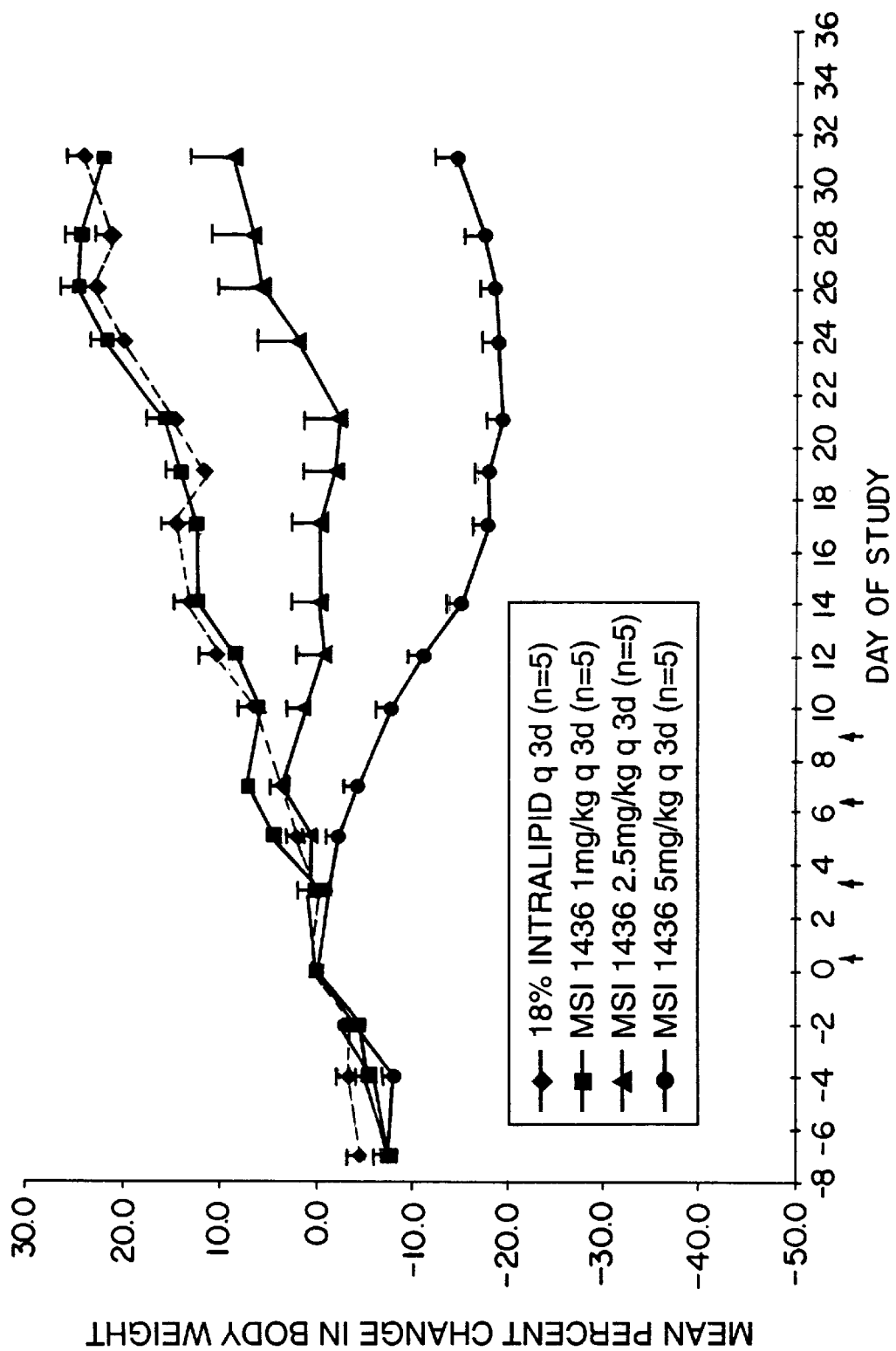
FIG. 26 shows the effect of 1436 on body weight in DBA/2J mice.
Figure 27:
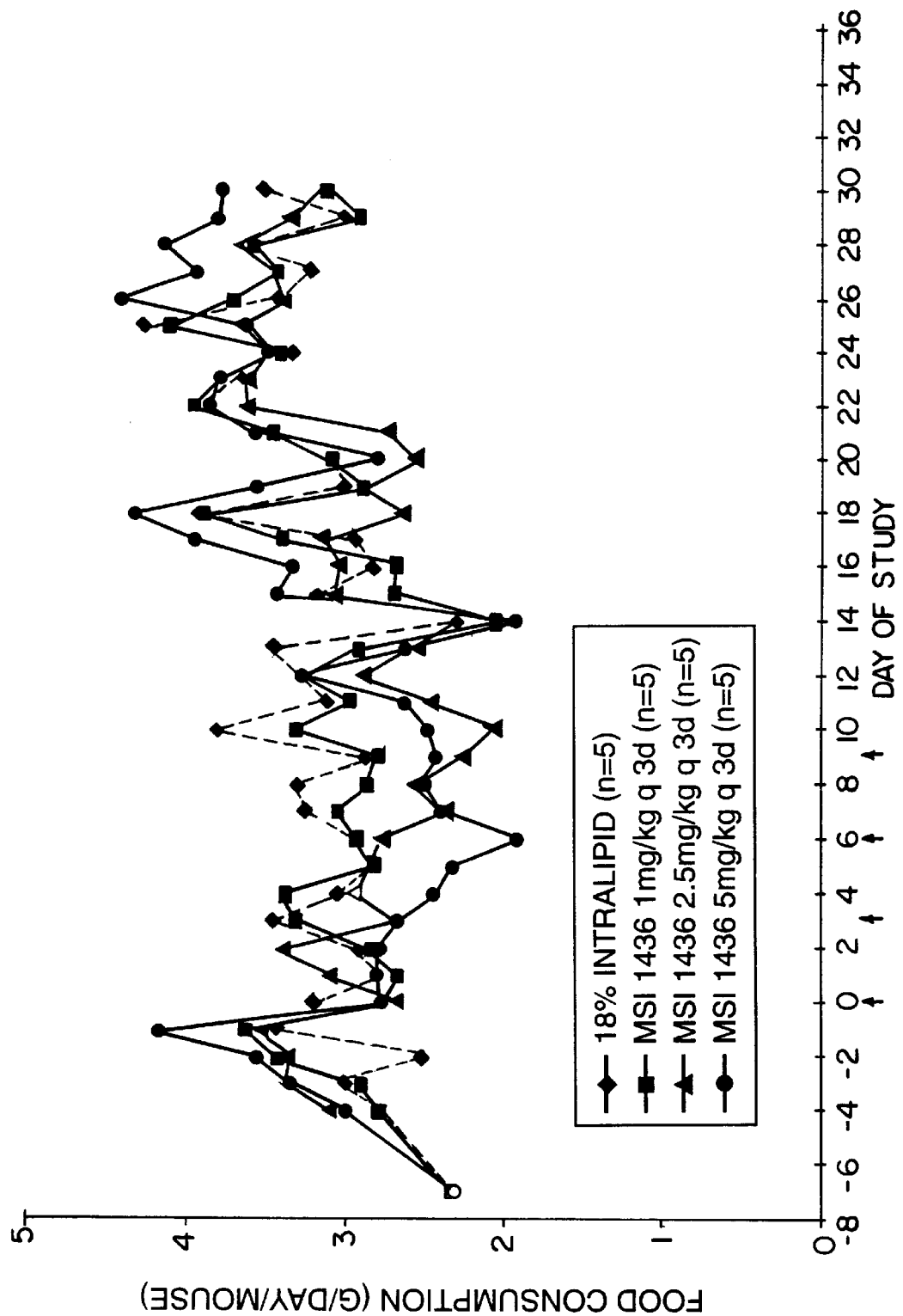
FIG. 27 shows the effect of 1436 on food consumption in DBA/2J mice.
Figure 28:
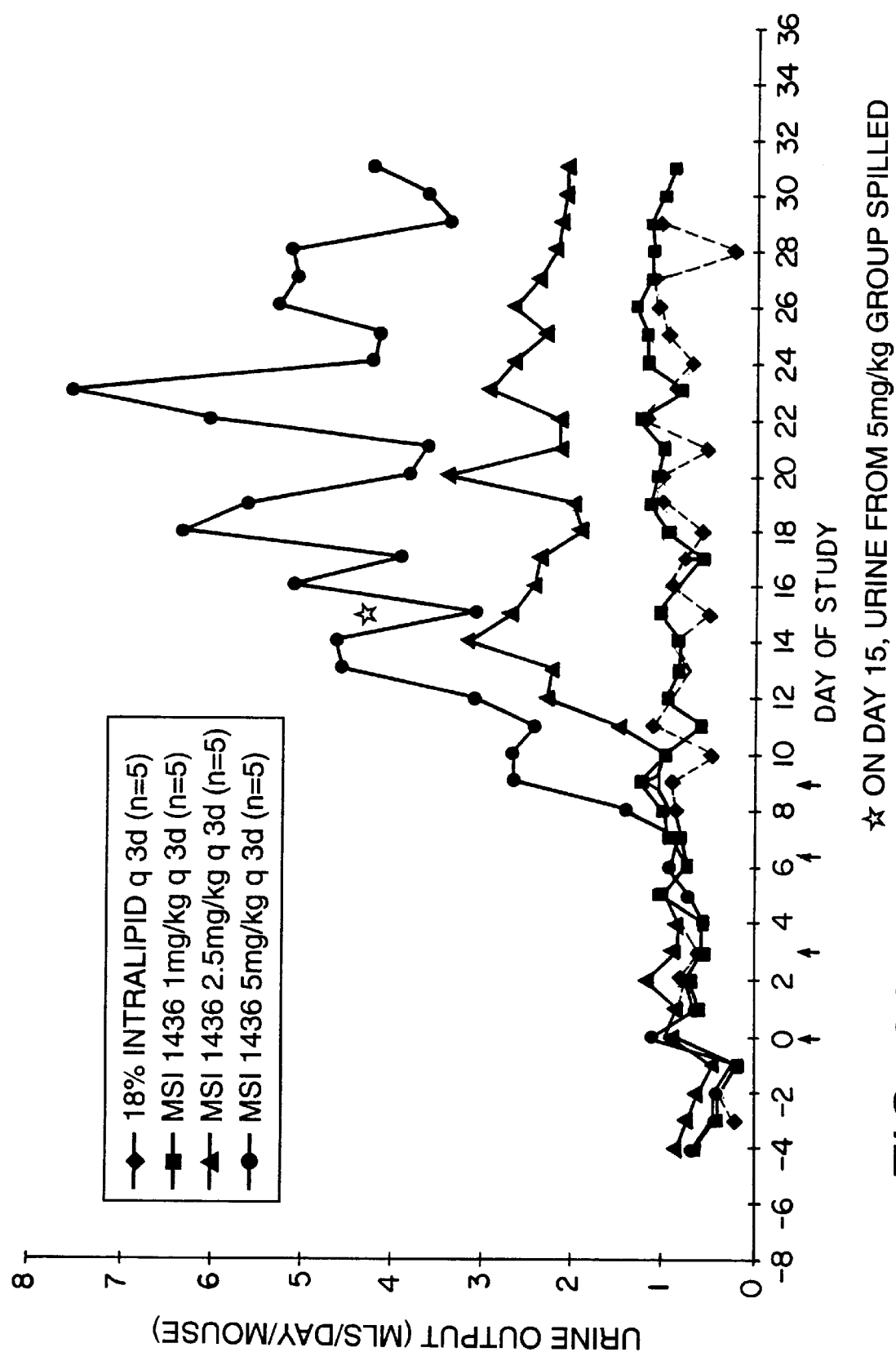
FIG. 28 shows the effect of 1436 on urine output in DBA/2J mice.
Figure 29:
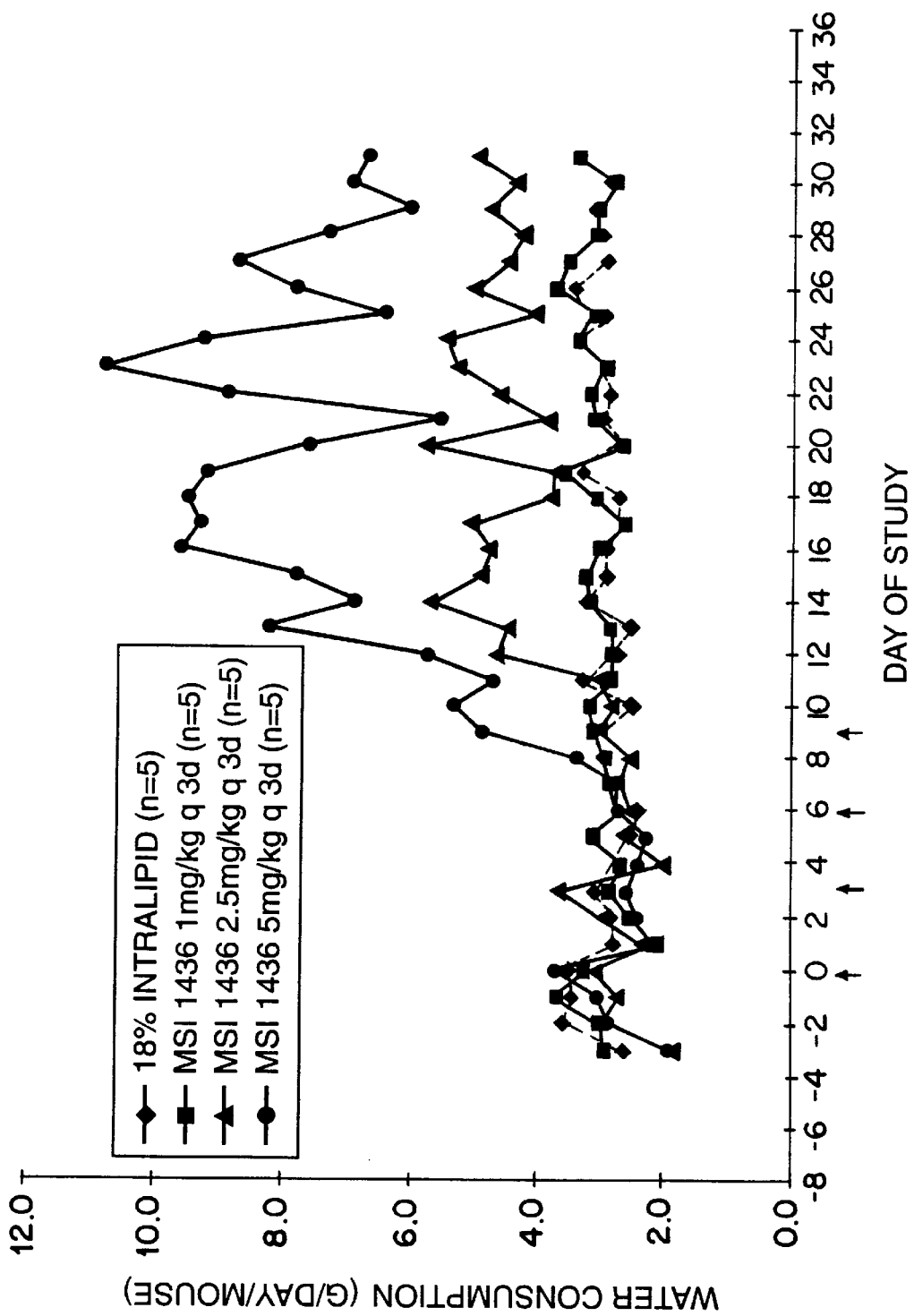
FIG. 29 shows the effect of 1436 on water consumption in DBA/2J mice.

To determine the roles of food and water consumption as well as urine output of compound 1436 on body weight suppression, 20 DBA/2J mice were randomly assigned to one of four groups (5 mice/group) that received either vehicle or compound 1436 at 1, 2.5, or 5 mg active/kg (i.p. every third day ("q 3d") for 4 dosings (i.e., dosed on Days 0, 3, 6 and 9)). Using metabolic cages for accurate measurements, group food consumption, group water consumption, and group urine output were measured daily, and individual body weight were monitored three times per week. FIG. 26 shows a dose-dependent change in body weight. FIG. 27 shows that food consumption of the group receiving compound 1436 at 5 mg/kg was lower than the other groups from Day 3 through Day 7 and lower than vehicle or low dose 1436 from Day 7 through 13. The mid-dose 1436 group had lower food consumption than control or low dose on Days 7 through 14. These reductions in food consumption preceded body weight loss by a few days; the lag would be consistent with a depletion of endogenous fuel storage (fat, glycogen, etc.). FIGS. 28 and 29 show a dose-dependent increase in urine output and water consumption that temporarily aligns with reductions in body weight. Water balance in the body is composed of intake via ingestion and formation of metabolic water and output is via urine, feces and insensible loss (perspiration, respiration). This study only measured water ingested and urine output so the animals may be in a negative water balance, even though water consumption was in excess of urine output. This study suggests that both food consumption as well as a diuresis (negative water balance) may contribute to the suppression of body weight.

Figure 30:
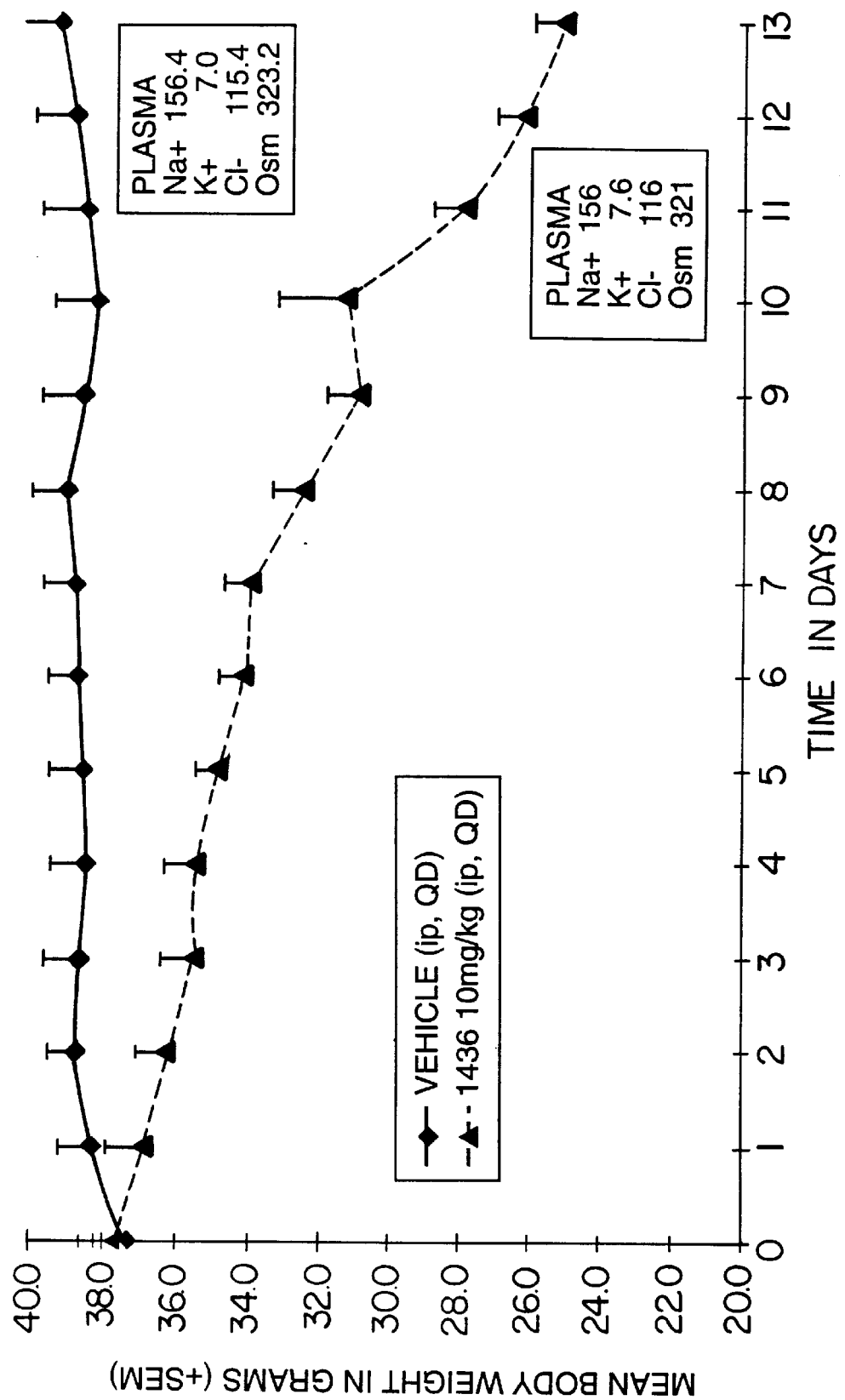
FIG. 30 shows the effect of 1436 on plasma levels of electrolytes and osmolality.

In a separate arm of study, 10 CD-1 mice (5 mice/group) were randomly assigned to receive either compound 1436 or vehicle as control administered intraperitoneally once per day, every day ("QD") for 13 days (Days 0 to 12). Body weights were monitored daily, and blood samples were obtained on Day 13 (one day post-last administration). Plasma levels of electrolytes (in mEq) and osmolality (in mOsm) were measured. The results in FIG. 30 show that compound 1436 caused weight loss without changing the isotonicity or electrolyte levels of plasma compared to vehicle control mice. Thus, 1436 meets a long-felt need for a diuretic agent that will cause fluid loss without a change in plasma isotonicity or electrolyte levels. All currently available diuretics perturb $K^+$ homeostasis. Discovery of a class of diuretics that is truly isokaluretic, i.e., neither increases nor decreases K+ excretion, has eluded researchers for decades (see Goodman & Gilman's *The Pharmacological Basis of Therapeutics*, Ninth Edition, 1996, p. 711).

Therapeutic Administration and Compositions

The mode of administration of compound 1436 and the other aminosterol compounds may be selected to suit the particular therapeutic use. Also, the compound can be administered to any subject for which treatment is believed to be beneficial, but administration to humans or other mammals is particularly preferred in the invention. Modes of administration generally include, but are not limited to, transdermal, intramuscular, intraperitoneal, intravenous, subcutaneous, intranasal, inhalation, intralesional, endothelial, and oral routes. The compounds may be administered by any convenient route, for example, by infusion or bolus injection, or by absorption through epithelial or mucocutaneous linings (e.g., oral mucosa, rectal, and intestinal mucosa, etc.), and the active 1436 ingredient may be administered together with other biologically active agents. Administration may be local or systemic.

In this application, the abbreviation "s.q." or "s.c." is used to represent subcutaneous administration of compound 1436 or other substances. The abbreviation "i.p." is used to represent intraperitoneal administration of compound 1436 or other substances. The abbreviation "i.v." is used to represent intravenous administration of compound 1436 or other substances. The abbreviation "i.m." is used to represent intramuscular administration of compound 1436 or other substances. In certain figures attached to this application, one graph axis is labeled "RT." This stands for "reverse transcriptase," which relates to the manner in which a viral enzyme can copy a RNA molecule into a DNA copy. Those skilled in the art are familiar with this measurement technique.

The present invention also provides pharmaceutical compositions that include compound 1436 or another aminosterol compound as an active ingredient. Such pharmaceutical compositions include a therapeutically effective amount of compound 1436 (or a pharmaceutically acceptable salt thereof) or another aminosterol compound (or a pharmaceutically acceptable salt thereof) and a pharmaceutically acceptable carrier or excipient. Examples of such a carrier include, but are not limited to, saline, buffered saline, dextrose, water, glycerol, ethanol, and combinations thereof. The particular form and formulation of the pharmaceutical composition should be selected to suit the mode of administration and can be determined and selected by the skilled artisan, e.g., through routine experimentation.

The pharmaceutical composition, if desired, also may contain minor amounts of other conventional agents, such as wetting or emulsifying agents, or pH buffering agents. The pharmaceutical composition may be in any suitable form, such as a liquid solution, suspension, emulsion, tablet, pill, capsule, sustained release formulation, or powder. The pharmaceutical composition also may be formulated as a suppository, with traditional binders and carriers, such as triglycerides. Oral formulations may include standard carriers, such as pharmaceutical grades of mannitol, lactose, starch, magnesium stearate, sodium saccharine, cellulose, magnesium carbonate, etc.

Various delivery systems are known and may be used to administer a therapeutic compound of the invention, e.g., encapsulation in liposomes, microparticles, microcapsules and the like.

In one embodiment, the pharmaceutical composition is formulated in accordance with routine procedures as a pharmaceutical composition adapted for intravenous administration to humans. Typically, compositions for intravenous administration are solutions in sterile isotonic aqueous buffer. Where necessary, the pharmaceutical composition also may include a solubilizing agent and a local anesthetic to ameliorate pain at the cite of the injection. Generally, the ingredients are supplied either separately or mixed together in unit dosage form, for example, as a dry lyophilized powder or water-free concentrate in a hermetically sealed container such as an ampule or sachette indicating the quantity of active agent. Where the pharmaceutical composition is to be administered by infusion, it may be dispensed with an infusion bottle containing sterile pharmaceutical grade water or saline. Where the pharmaceutical composition is administered by injection, an ampoule of sterile water for injection or saline may be provided so that the ingredients may be mixed prior to administration.

The amount of the therapeutic compound of the invention that will be effective in the treatment of a particular disorder or condition will depend on the nature of the disorder or condition, and this amount can be determined by standard clinical techniques known to those skilled in the art through routine experimentation. The precise dose to be employed in the pharmaceutical composition also will depend on the route of administration and the seriousness of the disease or disorder, and should be decided according to the judgement of the practitioner and each patient's circumstances. Effective therapeutical doses may be determined from extrapolations of dose-response curves derived from in vitro or animal-model test systems.

The following dosage ranges are exemplary. Suitable dosages for intravenous administration are generally about 20 micrograms to 40 milligrams of active compound per kilogram body weight. Suitable dosage ranges for intranasal administration are generally about 0.01 mg/kg body weight to 1 mg/kg body weight. Suitable dosage ranges for topical administration are generally at least about 0.01 % by weight. Suitable dosages for oral administration are generally about 500 micrograms to 800 milligrams per kilogram body weight, and preferably about 1–200 mg/kg body weight. Suppositories generally contain, as the active ingredient, 0.5 to 10% by weight of the aminosterol active ingredient. Oral formulations preferably contain 10% to 95% active ingredient.

Exemplary dosages of the aminosterol active ingredient for most pharmacological or therapeutical uses fall within the range of about 0.01 mg/kg body weight to about 100 mg/kg body weight. Preferred dosages are from 0.1 to 25 mg/kg body weight.

For subcutaneous administration, applicants have performed a pharmacokinetics study of the administration of compound 1436 in a mouse model. For this test, compound 1436 was administered s.q. at a dose of 10 mg/kg in mice. The peak 1436 concentration in the blood plasma from this 10 mg/kg dose was about 175 μg/ml after a time of about 2 hours. After 48 hours, the 1436 concentration is still about 10–15 μg/ml. This data indicates that relatively small 1436 doses may be used for s.q. administration. This data also provides an indication that oral dosing of 1436 will be effective.

The invention also may include a pharmaceutical pack or kit including one or more containers filled with pharmaceutical compositions in accordance with the invention. Associated with such containers may be a notice in the form prescribed by a government agency regulating the manufacture, use or sale of pharmaceuticals or biological products, which notice reflects approval by the agency of manufacture, use or sale for human administration.

By the term "effective amount" in this application, applicants refer to a suitable amount of the active ingredient of the invention, with an appropriate carrier or excipient, including a sufficient amount of the active ingredient to provide the desired effects or results. The effective amount can be readily ascertained by those skilled in the art through routine experimentation.

In describing the invention, applicant has stated certain theories in an effort to disclose how and why the invention works in the manner in which it works. These theories are set forth for informational purposes only. Applicants do not wish to be bound by any specific theory of operation.

While the invention has been described in terms of various specific preferred embodiments and specific examples, those skilled in the art will recognize that various changes and modifications can be made without departing from the spirit and scope of the invention, as defined in the appended claims.

I claim:

1. A method for suppressing appetite in a mammal, inhibiting growth factor production in a mammal, or inhibiting weight gain in a mammal, comprising the step of: administering an effective amount of a composition comprising a pharmaceutically acceptable carrier or excipient and an aminosterol compound according to the following formula:

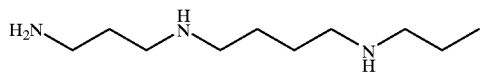

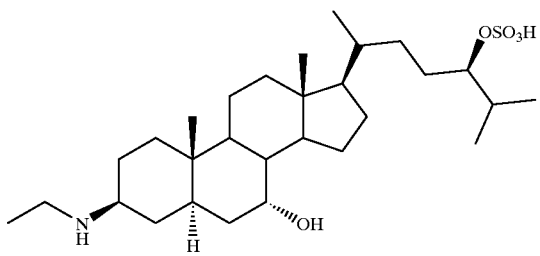

or a pharmaceutically acceptable salt thereof.

2. A method of claim 1, for suppressing appetite in a mammal comprising the step of: administering an effective amount of a composition comprising a pharmaceutically acceptable carrier or excipient and an aminosterol compound according to the following formula:

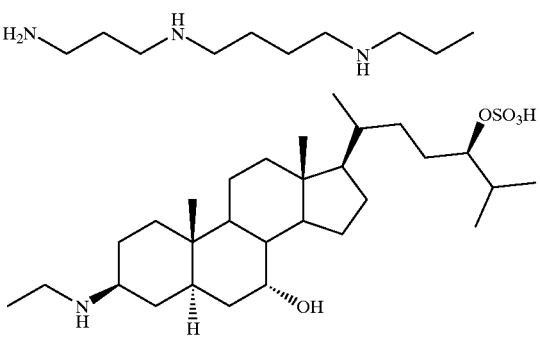

or a pharmaceutically acceptable salt thereof.

3. A method of claim 1 for inhibiting growth factor production in a mammal comprising the step of: administering an effective amount of a composition comprising a pharmaceutically acceptable carrier or excipient and an aminosterol compound according to the following formula:

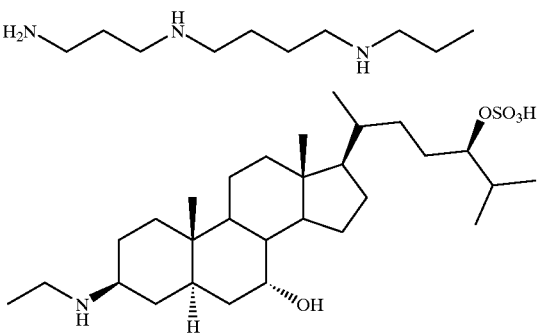

or a pharmaceutically acceptable salt thereof.

4. A method of claim 1 for inhibiting weight gain in a mammal, comprising the step of: administering an effective amount of a composition comprising a pharmaceutically acceptable carrier or excipient and an aminosterol compound according to the following formula:

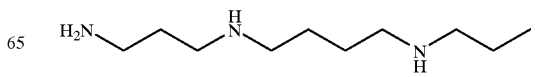

-continued

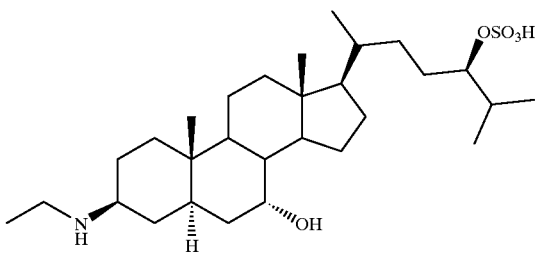

or a pharmaceutically acceptable salt thereof.

5. A method of claim 1, wherein the composition is administered in an amount from about 0.01 mg/kg of body weight/day to about 100 mg/kg of body weight/day.

6. A method of claim 5, wherein the composition is administered in an amount from about 0.1 mg/kg of body weight/day to about 25 mg/kg of body weight/day.

7. A method of claim 1, wherein the composition is in a formulation selected from the group consisting of: liquid solution, suspension, emulsion, tablet, pill, capsule, sustained release formulation, powder, suppository, oral formulation, liposome, microparticle, microcapsule, sterile isotonic aqueous buffer solution, and sterile isotonic aqueous buffer solution comprising anesthetic.

8. A method of claim 1, wherein the composition is administered transdermally, intramuscularly, intraperitoneally, intravenously, subcutaneously, intranasally, by inhalation, intralesionally, endothelially, topically, orally, by oral mucosa, rectally, or by intestinal mucosa.

9. A method of claim 8, wherein the composition is administered intravenously in an amount from about 20 µg of active compound per kilogram body weight to about 40 mg of active compound per kilogram body weight.

10. A method of claim 8, wherein the composition is administered intranasally in an amount from about 0.01 mg/kg of body weight/day to about 1 mg/kg of body weight/day.

11. A method of claim 8, wherein the composition is administered topically in an amount of at least about 0.01% by weight.

12. A method of claim 8, wherein the composition is administered orally in an amount from about 500 µg/kg of body weight/day to about 800 mg/kg of body weight/day.

13. A method of claim 12, wherein the composition is administered orally in an amount from about 1 mg/kg of body weight/day to about 200 mg/kg of body weight/day.

14. A method of claim 8, wherein the composition is administered as a suppository, wherein the suppository contains from about 0.5% by weight of the aminosterol active ingredient to about 10% by weight of the aminosterol active ingredient.

15. A method of claim 8, wherein the composition is administered subcutaneously in an amount from about from about 5 mg/kg of body weight/every third day to about 10 mg/kg of body weight/every third day.

16. A method for inhibiting weight gain or suppressing appetite in a mammal, comprising the step of: administering an effective amount of a composition comprising a pharmaceutically acceptable carrier or excipient and an aminosterol compound according to the following formula:

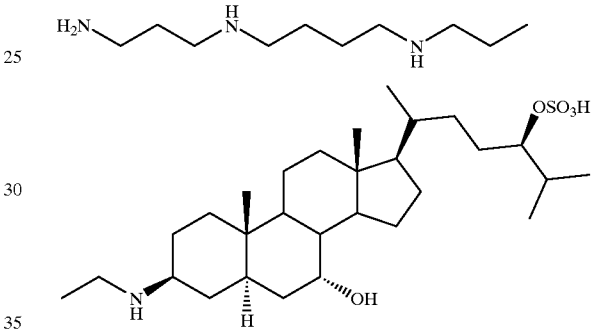

or a pharmaceutically acceptable salt thereof;

wherein the mammal does not experience fatigue.

* * * * *